US008568786B2

(12) United States Patent
Simone et al.

(10) Patent No.: US 8,568,786 B2
(45) Date of Patent: *Oct. 29, 2013

(54) METHOD AND COMPOSITIONS FOR POLYMER NANOCARRIERS CONTAINING THERAPEUTIC MOLECULES

(75) Inventors: Eric Simone, Philadelphia, PA (US); Vladimir R. Muzykantov, Warwick, PA (US); Thomas D. Dziubla, Lexington, KY (US)

(73) Assignee: The Trustees of the Universtiy of Pennsylvania, Philadelphia, PA (US)

( * ) Notice: Subject to any disclaimer, the term of this patent is extended or adjusted under 35 U.S.C. 154(b) by 404 days.

This patent is subject to a terminal disclaimer.

(21) Appl. No.: 12/739,584

(22) PCT Filed: Oct. 27, 2008

(86) PCT No.: PCT/US2008/081331
§ 371 (c)(1),
(2), (4) Date: Aug. 10, 2010

(87) PCT Pub. No.: WO2009/055794
PCT Pub. Date: Apr. 30, 2009

(65) Prior Publication Data
US 2010/0316571 A1 Dec. 16, 2010

Related U.S. Application Data

(63) Continuation-in-part of application No. 11/925,834, filed on Oct. 27, 2007, now Pat. No. 7,927,629.

(51) Int. Cl.
*A61K 49/00* (2006.01)
*A61K 38/00* (2006.01)
*A61K 9/14* (2006.01)
*A61K 38/43* (2006.01)
*C12Q 1/02* (2006.01)

(52) U.S. Cl.
USPC ......... 424/497; 424/499; 424/93.3; 424/94.1; 514/1.1; 435/29; 977/773; 977/906

(58) Field of Classification Search
None
See application file for complete search history.

(56) References Cited

U.S. PATENT DOCUMENTS

| 5,543,158 | A | 8/1996 | Gref et al. |
| 5,866,540 | A | 2/1999 | Jonczyk et al. |
| 6,007,845 | A | 12/1999 | Domb et al. |
| 7,597,907 | B2 | 10/2009 | Muzykantov |
| 2004/0001872 | A1 | 1/2004 | Shih et al. |
| 2004/0208929 | A1 | 10/2004 | Costantino |
| 2006/0073333 | A1 | 4/2006 | Anderson |
| 2006/0127386 | A1 | 6/2006 | Muzykantov et al. |
| 2009/0110741 | A1 | 4/2009 | Simone et al. |
| 2009/0258078 | A1 | 10/2009 | Muzykantov et al. |

FOREIGN PATENT DOCUMENTS

| WO | WO 98/32466 | 7/1998 |
| WO | WO 2009/055794 | 4/2009 |

OTHER PUBLICATIONS

Dziubla, Journal of Controlled release, 102, 2005.*
Roberts, Advanced Drug Delivery Reviews, 54, 2002.*
Geng, Polymer, 47, 2006.*
Ahmed, et al, "Self-porating polymersomes of PEG-PLA and PEG-PCL: hydrolysis-triggerted controlled release vesicles", Journal of Controlled Release, 96(1):37-53 (Apr. 2004).
Alakhov, et al., "Block copolymeric transport carriers as versatile vehicles for drug delivery", Expert Opinions on Investigational Drugs, 7(9):1453-1473 (Sep. 1998).
Atochina, et al., "Immunotargeting of catalase to ACE or ICAM-1 protects perfused rat lungs against oxidative stress", American Journal of Physiology Lung Cellular and Molecular Physiology, 275(4 pt 1):L806-L817 (Oct. 1998).
Avgoustakis, et al., "PGLA-mPEG particles of cisplatin: in vitro nanoparticle degredation, in vitro drug release and in vitro drug residence in blood properties", Journal of Controlled Release, 79(1-3):123-135 (Feb. 19, 2002).
Cai, et al., "Micelles of different morphology: advantages of worm-like filomicelles of PEO-PCL in paclitaxel delivery", Pharmaceutical Research, 24(11):2099-2109 (Nov. 2007; e-pub Jun. 13, 2007).
Champion, et al., "Role of target geometry in phagocytosis", Proceedings of the National Academy of Sciences USA, 103(13):4930-4934 (Mar. 28, 2006; e-pub Mar. 20, 2006).

(Continued)

*Primary Examiner* — Robert A Wax
*Assistant Examiner* — William Craigo
(74) *Attorney, Agent, or Firm* — Howson & Howson LLP

(57) ABSTRACT

A method of controlling a physical characteristic of polymeric nanocarrier-encapsulated protein particles includes altering or selecting a weight percentage of a hydrophobic polymer block in a total amphiphilic diblock copolymer of a primary emulsion of a double emulsion, freeze-thaw technique. The primary emulsion is formed using a freeze-thaw cycle of the amphiphilic diblock copolymer and a protein having a molecular weight of up to or equal to 300,000 Da. Selection of the hydrophobic polymer block percentage alters one or more characteristics of the resulting nanoparticles, such as shape. Thus, as one aspect, a method of producing filamentous polymeric nanocarrier-encapsulated protein (i.e., active enzyme) particles involves forming a primary emulsion using a freeze-thaw cycle of (i) an amphiphilic diblock copolymer, which has a molecular weight of about 10,000 to about 100,000 Da and comprises a conjugate of the hydrophobic polymer block and a hydrophilic polymer block, wherein the amphiphilic diblock copolymer comprises greater than 81% to about 95% by weight of the hydrophobic polymer block; and a protein having a molecular weight of up to or equal to about 300,000 Da. Various compositions comprising such filamentous-shaped nanocarrier particles, and methods of use for diagnosis and therapy are disclosed.

14 Claims, 13 Drawing Sheets

(56) References Cited

OTHER PUBLICATIONS

Christofidou-Solomidou, et al., "PECAM—directed delivery of catalase to endothelium protects against pulmonary vascular oxidative stress", American Journal of Physiology Lung Cellular and Molecular Physiology, 285(2):L283-L292 (Aug. 2003).
Discher, et al, "Polymer vesicles", Science, 297(5583):967-973 (Aug. 9, 2002).
Dziubla, et al., "Endothelial targeting of semi-permeable polymer nanocarriers for enzyme therapies", Biomaterials, 29(2):215-227 (Jan. 2008; e-pub Oct. 24, 2007).
Dziubla, et al., "Polymer nanocarriers protecting enzyme cargo against proteolysis", Journal of Controlled Release, 102(2):427-439 (Feb. 2, 2005; e-pub Nov. 19, 2004).
Garnacho, et al., "Delivery of acid sphingomyelinase in normal and Niemann-Pick disease mice using ICAM-1-targeted polymer nanocarriers", Journal of Pharmacology and Experimental Therapeutics, 352(2):400-408 (May 2008; e-pub Feb. 20, 2008).
Geng, et al., "Shape effects of filaments versus spherical particles in flow and drug delivery", Nature Nanotechnology, 2(4):249-255 (Mar. 25, 2007).
Geng, et al., "Visualization of degradable worm micelle breakdown in relation to drug release", Polymer, 47(7):2519-2525 (Feb. 7, 2006).
Gopferich, A., "Polymer Bulk Erosion", Macromolecules, 30(9):2598-2604 (Apr. 1, 1997).
Hansen, et al. "Attachment of antibodies to sterically stablized liposomes: evaluation, comparison and optimization of coupling procedures", Biochimica et Biophysica Acta, 1239(2):133-144 (Nov. 1, 1995).
Kozower, et al., "Immunotargeting catalase to the pulmonary endothelium alleviates oxidative stress and reduces acute lung transplantation injury", Nature Biotechnology, 21(4):392-398 (Apr. 2003; e-pub Mar. 24, 2003).
Langer, R., "Drug Delivery and Targeting", Nature, 392(6679 Suppl):5-10 (Apr. 30, 1998).
Lasic, D. D., "Doxorubicin in sterically stabilized lysosomes", Nature, 380(6574):561 (Apr. 11, 1996).
Li et al, "PEGylated PLGA nanoparticles as protein carriers: synthesis, preparation and biodistribution in rate, Journal of Controlled Release", 71(2):203-211 (Apr. 2001).
McCord, J.M., "Superoxide dismutase on aging and disease: an overview", Methods in Enzymology, 349:331-341 (2002).
Moghimi, et al., "Stealth Liposomes and Long Circulating Nanoparticles: Critical issues in pharmacokinetics, opsonization and protein-binding properties", Progress in Lipid Research, 42(6):463-478 (Nov. 2003).
Muro, et al., "Slow intracellular trafficking of catalase nanoparticles targeted to ICAM-1 protects endothelial cells from oxidative stress", American Journal of Physiology Cell Physiology, 285(5):C1339-C1347 (Nov. 2003; e-pub Jul. 23, 2003).
Muzykantov, et al, "Streptavidin facilitates internalization and pulmonary targeting of an anti-endothelial cell antibody (platelet-endothelial cell adhesion molecule 1): a strategy for vascular immunotargeting of drugs", Proceedings of the National Academy of Sciences USA, 96(5):2379-2384 (Mar. 1999).
Muzykantov, et al., "Immunotargeting of antioxidant enxymes to the pulmonary endothelium", Proceedings of the National Academy of Sciences USA, 93(11):5213-5218 (May 1996).
Muzykantov, "Targeting of superoxide dismutase and catalase to vascular endothelium", Journal of Controlled Release, 71(1): 1-21 (Mar. 12, 2001).
Ravenelle, et al., "Self-Assembly of Poly([R]-3-hydroxybutyric acid)-Block-Poly(ethylene glycol) Diblock Copolymers", Biomacromolecules, 4(3):856-858 (May-Jun. 2003).
Roux, et al., "On the characterization of pH sensitive liposome/polymer complexes", Biomacromolecules, 4(2):240-248 (Mar.-Apr. 2003).
Shuvaev, et al., "Factors modulating the delivery and effect of enzymatic cargo conjugated with antibodies targeted to the pulmonary endothelium", Journal of Controlled Release, 118(2):235-244 (Apr. 2, 2007; e-pub Jan. 8, 2007).
Simone, et al., "Effect of Polymer Amphiphilicity on Loading of a Therapeutic Enzyme into Protective Filamentous and Spherical Polymer Nanocarriers", Biomacromolecules, 8(12):3914-3921 (Dec. 2007; e-pub Nov. 27, 2007).
Son, et al., "Template synthesis of multifunctional nanotubes for controlled release", Journal of Controlled Release, 114(2):143-152 (Aug. 28, 2006; e-pub Jun. 7, 2006).
Sweitzer, et al., "PECAM directed immunotargeting of catalase: specific, rapid and transient protection against hydrogen peroxide", Free Radical Biology & Medicine, 34(8):1035-1046 (Apr. 15, 2003).
Vinogradov, et al., "Self-Assembly of Polyamine-Poly(ethylene glycol) Copolymers with Phosphorothioate Oligonucleotides", Bioconjugate Chemistry, 9(6):805-812 (Nov.-Dec. 1998).
Von Burkersroda, et al., "Why degradable polymers undergo surface erosion or bulk erosion", Biomaterials, 23(21):4221-4231 (Nov. 2002).
Wiewrodt, et al., "Size-dependent intracellular immunotargeting of therapeutic cargoes into endothelial cells", Blood, 99(3):912-922 (Feb. 1, 2002).
Wu, et al., "Neuroprotection with noninvasive neurotrophin deliver to the brain", Proceedings of the National Academy of Sciences USA, 96(1):254-259 (Jan. 5, 1999).
Zambaux, et al., "Protein-C loaded monomethoxypoly (ethylene oxide)-poly(lactic acid) nanoparticles", International Journal of Pharmaceutics, 212(1):1-9 (Jan. 5, 2001).
Zhang, et al., "Micellization Phenomena of Amphiphilic Block Copolymers Based on Methoxy Poly(ethylene glycol) and Either Crystalline or Amorphous Poly(caprolactone-b-lactide)", Biomacromolecules, 7(9):2492-2500 (Sep. 2006).
Zhang, et al., "Multiple morphologies of "crew cut" aggregates of polystyrene-b-poly(acrylic acid) block copolymers", Science, 268(5218):1728-1731 (Jun. 23, 1995).
International Preliminary Report on Patentability dated May 6, 2010 issued in International Patent Application No. PCT/US2008/081331.
International Search Report dated Dec. 8, 2008 issued in International Patent Application No. PCT/US2008/081331.
Office Action dated Aug. 14, 2008 in U.S. Appl. No. 11/266,785.
Response to Office Action dated Nov. 14, 2008 in U.S. Appl. No. 11/266,785.
Examiner's Amendment with Notice of Allowance dated Mar. 6, 2009 in U.S. Appl. No. 11/266,785.
Office Action dated Jun. 28, 2010 in U.S. Appl. No. 11/925,834.
Office Action dated Jan. 26, 2010 in U.S. Appl. No. 11/925,834.
Response to Office Action dated Apr. 7, 2010 in U.S. Appl. No. 11/925,834.

* cited by examiner

Fig. 4A  Fig. 4B
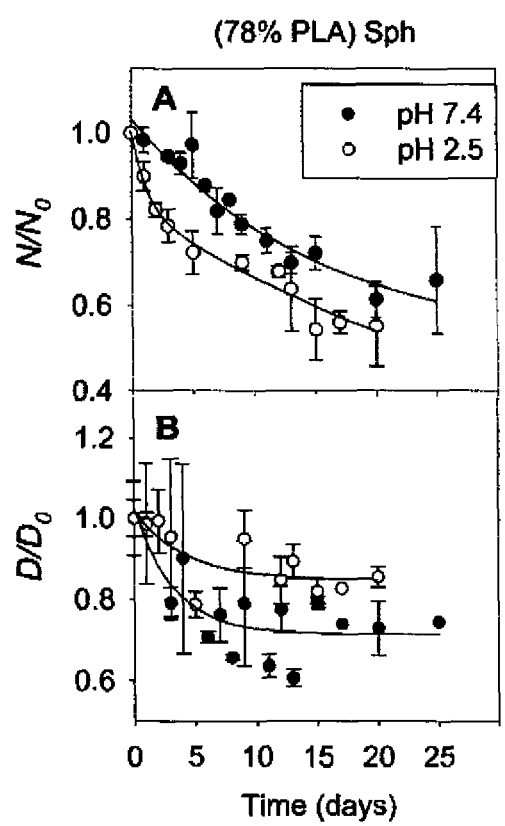
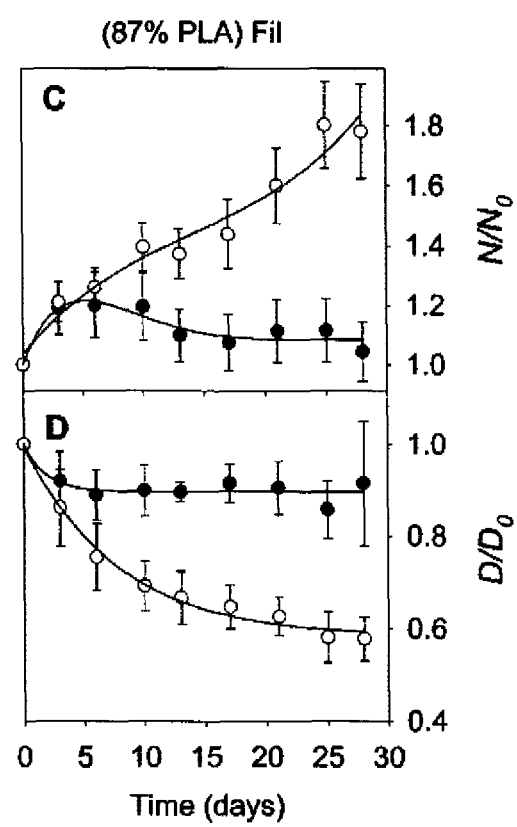
Fig. 4C  Fig. 4D

METHOD AND COMPOSITIONS FOR POLYMER NANOCARRIERS CONTAINING THERAPEUTIC MOLECULES

STATEMENT REGARDING FEDERALLY SPONSORED RESEARCH OR DEVELOPMENT

The present invention was supported by Grant Nos. HL007954, HL073940-01-A1, PO1-HL079063 from the National Institutes of Health. The government has an interest in the invention.

CROSS-REFERENCE TO OTHER APPLICATIONS

This application is a U.S. national stage of international patent application No. PCT/US2008/081331, filed Oct. 27, 2008, which claims the benefit of the priority of pending non-provisional U.S. patent application Ser. No. 11/925,834, filed Oct. 27, 2007. Both the international and non-provisional patent applications are incorporated herein by reference.

BACKGROUND OF THE INVENTION

Rapid clearance from the circulation, inactivation by nascent proteases and inhibitors, and a lack of affinity for the desired target sites of action limit the utility of potent but labile therapeutic proteins (Muzykantov, V. R., *J Control Release* 2001, 71, (1), 1-21). Diverse drug delivery systems (e.g., natural lipoproteins, liposomes and polymer nanocarriers) are being widely designed in order to maximize drug efficacy and minimize side effects (Langer, R., *Nature* 1998, 392, (6679 Suppl), 5-10). For example, polyethylene glycol (PEG), a hydrophilic polymer that enhances aqueous solubility, masks drugs and carriers from host defense systems and prolongs circulation in the bloodstream ("stealth" technology) (Moghimi, S. M. et al, *Prog Lipid Res* 2003, 42, (6), 463-78; Roux, E. et al, *Biomacromolecules* 2003, 4, (2), 240-248). Nanocarriers coated with PEG are already in clinical use for the intravascular delivery of anti-tumor agents, in the form of stealth liposomes (e.g., Doxil®) (Lasic, D. D., *Nature* 1996, 380, (6574), 561).

Comparatively little effort has been invested, however, in nanocarrier mediated delivery of therapeutic proteins, which are complicated because activity requires maintaining the protein's native folded state. Loading such therapeutic proteins into biodegradable polymer nanocarriers (PNC) to protect proteins and extend therapeutic duration can be complicated by protein unfolding and inactivation. Loss of enzymatic activity due to protein unfolding in harsh conditions of PNC formulation has represented a major barrier to the use of biodegradable co-polymers for delivery of therapeutic enzymes.

Formulations based on synthetic amphiphilic copolymers that consist of hydrophobic blocks with hydrophilic PEG blocks yield a variety of aggregate shapes, namely micelles, vesicles and frozen particles—a versatile palette of polymer nanocarriers with further diversity in size and degradation patterns (Discher, D. E. et al, *Science* 2002, 297, (5583), 967-73; Zhang, J. et al., *Biomacromolecules* 2006, 7, (9), 2492-2500; Vinogradov, S. V., et al, *Bioconjug Chem* 1998, 9, (6), 805-12; Discher, D. E. et al, 2002, cited above; Ravenelle, F. et al, *Biomacromolecules* 2003, 4, (3), 856-858; Zhang, L.; Eisenberg, A., *Science* 1995, 268, (5218), 1728-1731; and Alakhov, V. Y. et al, *Expert Opin Investig Drugs* 1998, 7, (9), 1453-73).

A relatively mild freeze-thaw double emulsion method for the encapsulation of active catalase, a large 249 kDa tetrameric enzyme, into PEG-PL(G)A (poly lactic-co-glycolic acid) PNC is discussed in US Patent Application Publication No. 2006/0127386. PLGA is a biodegradable FDA-approved co-polymer used for the production of drug delivery systems and sutures. Furthermore, $H_2O_2$, a reactive oxygen species widely implicated in the pathogenesis of many disease conditions (Muzykantov 2001, cited above) is freely diffusible through PL(G)A (Dziubla, T. D.; et al, *J Control Release* 2005, 102, (2), 427-39). Catalase encapsulated within PEG-PL(G)A PNC as discussed in the preceding three publications was protected from proteolysis and decomposed $H_2O_2$ diffusing through the PNC shell. The freeze thaw cycle added during the primary emulsion enhanced catalase loading into PNC and reduced its formulation-induced inactivation.

Despite the specificity of therapeutic enzymes, medical utility is often limited by inadequate delivery and insufficient stability in the body. Catalase is a naturally occurring antioxidant enzyme that can be used for the treatment of vascular oxidative stress involved in the pathogenesis of many disease conditions (Muzykantov 2001, cited above). However, catalase and other antioxidant enzymes (e.g., superoxide dismutase) have no practical medical utility due to inadequate delivery to therapeutic sites, especially the endothelial cells lining the luminal surface of blood vessels. Conjugation of enzymes to targeting antibodies improves delivery and effects of antioxidant enzymes in diverse animal models (Christofidou-Solomidou, M. et al, *Am J Physiol Lung Cell Mol Physiol* 2003, 285, (2), L283-92; Kozower, B. D. et al, *Nat Biotechnol* 2003, 21, (4), 392-8), and yet therapeutic duration is limited to a few hours by catalase proteolysis at the target site (Muro, S. et al, *Am J Physiol Cell Physiol* 2003, 285, (5), 01339-47).

There remains a need in the art for improved compositions and methods for targeting active therapeutic proteins to cells which maintains folded and active protein, provides protection of the proteins from subsequent cellular degradation, and prolongs their release in vivo.

SUMMARY OF THE INVENTION

In one aspect, a method of controlling a physical characteristic of polymeric nanocarrier-encapsulated protein particles is disclosed. The method includes altering or selecting a weight percentage of a hydrophobic polymer block in a total amphiphilic diblock copolymer of a primary emulsion. The primary emulsion is formed using a freeze-thaw cycle of: (i) the amphiphilic diblock copolymer, which has a molecular weight of about 10,000 to about 100,000 Da and is a conjugate of the hydrophobic polymer block and a hydrophilic polymer block; and (ii) a protein having a molecular weight of up to or equal to 300,000 Da. A secondary emulsion is formed from the primary emulsion. The particles having the selected characteristics are recovered from this method. According to this method, the size and shape of the protein composition and protection of the protein against external proteolysis and mechanism of degradation of the nanocarriers are controlled by the weight percentage of the hydrophobic polymer block in the total amphiphilic diblock copolymer. Thus, in one embodiment, the weight percentage of hydrophobic polymer block in a total amphiphilic diblock copolymer of the primary emulsion is about 60% to less than 80% by weight of the hydrophobic polymer block, resulting in polymeric nanocarrier-encapsulated protein particles of primarily spherical shape. In another embodiment, the weight percentage of hydrophobic polymer block in a total amphiphilic diblock copolymer of the primary emulsion is from 80% to less than 81% by weight of the hydrophobic polymer block, resulting in a mixture of spherical and filamentous shapes of polymeric nanocarrier-encapsulated protein particles.

In another aspect, a method of producing primarily all filamentous polymeric nanocarrier-encapsulated protein particles includes forming a primary emulsion using a freeze-thaw cycle of (i) an amphiphilic diblock copolymer, which has a molecular weight of about 10,000 to about 100,000 Da and comprises a conjugate of the hydrophobic polymer block and a hydrophilic polymer block, wherein the amphiphilic diblock copolymer contains greater than 81% to about 95% by weight of the hydrophobic polymer block; and (ii) a protein having a molecular weight of up to or equal to about 300,000 Da. A secondary emulsion is formed from the primary emulsion. Recovery of primarily filamentous particles is permitted by this method.

In another aspect, a composition of polymeric nanocarrier-encapsulated protein particles is provided. The compositions contains (a) a protein having a molecular weight of up to or equal to about 300,000 Da; (b) an amphiphilic diblock copolymer having a molecular weight of about 10,000 to about 100,000 Da and which is a conjugate of a hydrophilic polymer block and a hydrophobic polymer block, wherein the total amphiphilic diblock copolymer is greater than about 80% by weight of the hydrophobic polymer block. This composition contains filamentous-shaped nanocarrier particles. In one embodiment, wherein the total amphiphilic diblock copolymer comprises between 80-81% by weight of the hydrophobic polymer block, the composition comprises a mixture of spherical shaped particles and filamentous particles. In another embodiment, wherein the total amphiphilic diblock copolymer comprises between 82 to 95% by weight of the hydrophobic polymer block, the composition comprises primarily all filamentous particles.

In still another aspect, a pharmaceutical composition contains the filamentous polymeric nanocarrier-encapsulated protein particles in which the encapsulated protein is a therapeutically useful protein. In one such embodiment, such a protein is a therapeutically useful enzyme.

In another aspect, a drug delivery vehicle comprises the filamentous polymeric nanocarrier-encapsulated protein particles of this invention.

In still another aspect, a pharmaceutical composition comprises the mixed spherical/filamentous polymeric nanocarrier-encapsulated protein particles in which the encapsulated protein is a therapeutically useful protein. In one such embodiment, such a protein is a therapeutically useful enzyme.

In another aspect, a composition of polymeric nanocarrier-encapsulated protein particles is provided, which comprises (a) a protein having a molecular weight of up to or equal to about 300,000 Da; (b) an amphiphilic diblock copolymer having a molecular weight of about 10,000 to about 100,000 Da and comprising a conjugate of a hydrophilic polymer block and a hydrophobic polymer block, wherein the total amphiphilic diblock copolymer comprises about 60 to 80% by weight of the hydrophobic polymer block. This composition comprises spherical particles with diameters of about 250 to 400 nm.

In still another aspect, a pharmaceutical composition comprises the spherical polymeric nanocarrier-encapsulated protein particles in which the encapsulated protein is a therapeutically useful protein. In one such embodiment, such a protein is a therapeutically useful enzyme.

In still another aspect, the particles in the composition have affinity moieties on the outer surfaces thereof, such as an antibody to a cell adhesion molecule.

In yet a further aspect, a diagnostic or therapeutic method is provided which comprises administering to a mammalian subject or tissue thereof in vivo, ex vivo or in vitro, one of the pharmaceutical compositions described above.

In another aspect, a diagnostic or therapeutic method is described comprising administering to a mammalian subject or tissue thereof in vivo, ex vivo or in vitro, a composition or particle produced by any of the methods described herein. These compositions are preferably produced by a double emulsion formulation without inactivation of the encapsulated protein.

Other aspects and advantages are provided in the following detailed description.

BRIEF DESCRIPTION OF THE FIGURES

FIG. 2A is a graph showing that loading by mass is defined as protein mass in PNC divided by the total amount of protein added to the particle preparation during the freeze-thaw modified double emulsion formulation. FIG. 2B is a graph showing that enzyme inactivation increased at the higher ranges of PLA % in the formulation. FIG. 2C is a graph showing enzymatic activity of catalase lost during the formulation homogenizations, based on kinetics of $H_2O_2$ degradation. Percent of activity of total protein mass added is shown. The greatest enzyme protection from formulation occurs between 63 and 84 wt % of the hydrophobic block polymer, e.g., PLA. Loading of catalase into mPEG-PLA PNC was based on enzymatic activity. For all figures, MW region with % PLA<60% was omitted due to negligible PNC content by polymer mass.

FIG. 3A shows that activity of free catalase is practically eradicated after 1 hour of incubation with pronase. Activity of PNC-loaded catalase decreases by ~70% after five hours of incubation and stabilizes afterwards. Inset illustrates the concept of a PNC "protective cage" which is impermeable to proteases, yet freely permeable to the encapsulated enzyme substrate, $H_2O_2$. FIG. 3B is a graph showing diverse % PLA PNC loaded with $^{125}$I-catalase were incubated with pronase for 1 hr and degraded protein was separated from protected/encapsulated protein by centrifugation. This measure has been shown to correlate linearly with preservation of enzymatic activity.

FIG. 4A shows the degradation of spherical (78% PLA) PNC by DLS as total number of PNC over time. FIG. 4B shows the degradation of spherical (78% PLA) PNC by DLS as effective diameter plotted against time. A bulk erosion phenomenon is evident from a decrease in the total number of PNC of FIG. 4A accompanied by a relatively constant measure in effective diameter. FIG. 4C shows the degradation of filamentous PNC (87% PLA) by DLS as total number of PNC plotted against time. FIG. 4D shows the degradation of filamentous PNC (87% PLA) by DLS as diameter of PNC plotted against time. Change in diameter of filamentous PNC is heightened at pH 2.5, while little change is seen at either neutral pH or pH 5.0 (data not shown). Effective diameters correlate with hydrodynamic volume occupied by filamentous PNC, which are coiled in solution as verified by fluorescence microscopy. Concomitant with a decrease in diameter was an increase in number of filamentous PNC in FIG. 4C. Similar trends were observed with higher MW (93% PLA) filamentous PNC.

FIG. 7A is a bar graph showing results of circulation studies of PEG-catalase (black bars) and unmodified catalase (white bars). % ID indicates percent injected dose. FIG. 7B is a graph showing concentration dependence of enzyme resistance to inactivation by a model protease. Catalase at 0.02 wt % (○) or 0.2 wt % (●) and PEG-catalase 0.02 wt % (△) or 0.2 wt % (▲). Data are shown as mean value±standard deviation. * indicates statistically significant differences (P<0.05).

FIG. 8A shows loading by mass, defined as protein mass in PNC divided by the total amount added to the particle prep during the modified emulsion formulation. FIG. 8B shows the enzymatic activity of catalase lost during the formulation, based on kinetics of $H_2O_2$ degradation. Percent of activity of total protein mass added is shown. FIG. 8C shows loading of catalase into mPEG-PLA PNC based on enzymatic activity. Black bars indicate PEG-catalase loading, while gray bars are unmodified catalase loading. Fil refers to filamentous PNC and sph refers to spherical PNC.

FIG. 9A shows sizing of spherical PNC loaded with either catalase (black) or PEG-catalase (gray) as determined by DLS. FIG. 9B shows mass yield of PNC as determined by PLA content and all particle preps were re-suspended in 1 ml PBS FIG. 10A shows the protective effect against external protease degradation of PNC-loaded enzymes, either PEG-catalase loaded PNC (black) or catalase loaded PNC (gray). Non-loaded (far left bars) refers to enzyme incubated with empty PNC. FIG. 10B shows circulation of PEG-catalase-PNC (black) and unmodified catalase-PNC (gray) where % ID represents the percent of injected dose remaining in the bloodstream. * indicates a statistically significant difference between PEG-catalase-PNC and catalase-PNC, while # indicates a statistically significant difference between both PNC preparations and unloaded catalase (dashed line).

FIG. 12A is a graph summary of the average contour lengths of each f-PNC, as a function of polymer MW. Contour length is the absolute length, as traced along the filament backbone. FIG. 12 B is a histogram indicating the contour length distribution for preparation EL2-10. FIG. 12 C is a histogram indicating the contour length distribution for preparation EL5-27. FIG. 12 D is a histogram indicating the contour length distribution for preparation EL10-40. FIG. 12 E is a histogram indicating the contour length distribution for preparation EL19-70. All values shown are average±SEM.

FIG. 14A shows cross sectional diameters, d, that were determined from TEM image analysis. Inset shows the results of a line scan across an example EL10-40 f-PNC.

FIG. 15A shows loading efficiency or percent mass loading denotes the amount of catalase loaded relative to the amount added. FIG. 15B shows percent protection indicating the amount off-PNC-encapsulated catalase that is resistant to proteolytic degradation after a one hour incubation with the non-specific protease, pronase. Non-encapsulated, i.e., surface adsorbed, catalase exhibits less than 5% protection within one hour. Mass yield concentration of f-PNC by colorimetric assay for polymer content is shown in the inset. FIG. 15C illustrates the percent initial activity as the amount of enzymatic activity retained, post formulation. All f-PNC preparations were spun down and re-suspended in 1 ml PBS before mass determination. A 100% yield would be 25 mg/ml. % Activity loading is the amount of catalase activity loaded within the f-PNC, relative to the amount added during the formulation.

DETAILED DESCRIPTION OF THE INVENTION

Figures 1A, 1B:
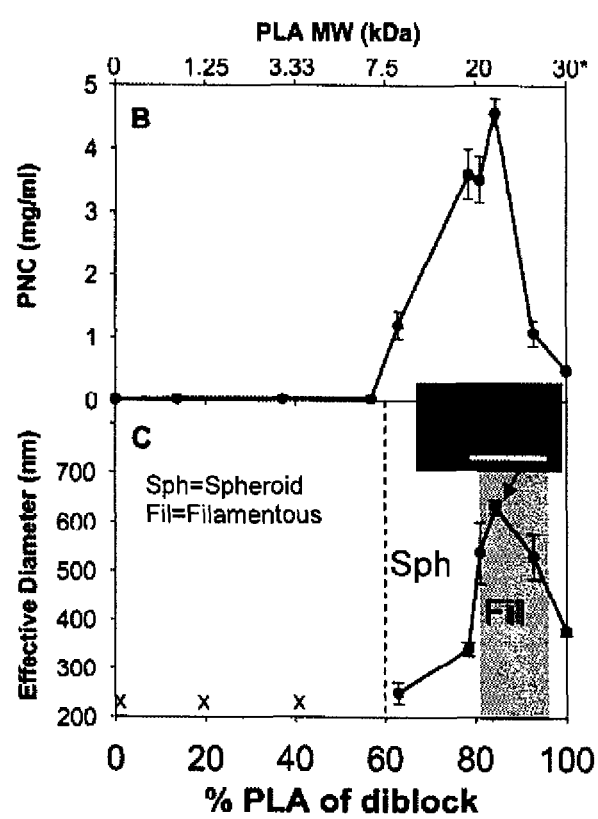
FIG. 1A is a graph showing that mass yield of PNC was determined by the hydrophobic block polymer (e.g., PLA) content in the diblock copolymer. All particle preparations were re-suspended in 1 ml phosphate buffered saline (PBS).
FIG. 1B is a graph showing that sizing was determined by dynamic light scattering (DLS). "Sph" indicates the spheroid PNC range, while "Fil" notes the filamentous PNC range. Shades of gray denote PLA percent providing formulation of spherical (white), filamentous (gray) and mixed (light grey) geometries of PNC. Inset shows confocal fluorescent microscopy image of filamentous 84% PLA PNC. Staining was performed with the lipophilic carbocyanine dye, PKH26, intercalated into the PNC polymer. Scale bar is 5 μm. Data are shown as mean value±standard deviation.

The above-stated needs in the art are met by the following described compositions and methods for novel delivery systems that can accommodate large molecular weight therapeutic and diagnostic proteins. The following compositions and methods are based upon the inventors' discovery that for polymeric nanocarriers (PNC) composed of a hydrophobic polymer block and a hydrophilic polymer block, the percentage by weight of the hydrophobic polymer block to the total weight of the diblock copolymer is a key parameter that governs PNC assembly, geometry and stability, as well as enzyme loading, activity and subsequent protection against proteolysis. Through control of molecular weight composition, the methods and compositions described herein can, in one embodiment, produce filamentous carriers containing enzyme cargo that is protected from proteolysis. By balancing the amphiphilic character of the PNC, the methods and compositions provide a nanocarrier well suited for the prolonged delivery of enzymes and other proteins.

Thus, in one aspect, a method of controlling a physical characteristic of polymeric nanocarrier-encapsulated protein particles involves altering or selecting a weight percentage of a hydrophobic polymer block in a total amphiphilic diblock copolymer used in a freeze-thaw modified double emulsion method of forming a polymeric nanocarrier (PNC). Embodiments of suitable double emulsion methods are described in Dziubla 2005, cited above; and U.S. Patent Application Publication No. 2006/0127386, incorporated herein by reference. The homogenization in the double emulsion formulation produces PNC of desired size (200-500 nm), yet also reduces enzyme activity and decreases loading of the enzyme drug. The freeze-thaw cycle aids synthesis of enzyme-loaded PNC by both enhancing the amount of loaded enzyme and protecting it from inactivation (Dziubla et al 2005, cited above).

The method involves the steps of homogenizing at least one protein and the amphiphilic diblock copolymer solution at subzero temperature so that a primary emulsion is formed, mixing the emulsion with an aqueous phase, homogenizing the mixture to form a secondary emulsion and recovering a polymeric nanocarrier-encapsulated protein composition therefrom. The inventors have discovered that a physical characteristic such as one or more of: the size of the polymeric nanocarrier-encapsulated protein particles, the shape of the polymeric nanocarrier-encapsulated protein particles, the protection of the protein against external proteolysis, and the mechanism of degradation of the polymeric nanocarrier-encapsulated protein particles can be desirably generated in such a method when the actual weight % of the hydrophobic polymer block $\overline{M_n}$ to the entire diblock copolymer $\overline{M_n}$ is adjusted as discussed herein.

As supported in the examples below, the inventors encapsulated an exemplary active enzyme into an exemplary amphiphilic diblock copolymer (e.g., methoxy-poly(ethylene glycol-block-lactic acid) (mPEG-PLA) PNC, with a freeze-thaw double emulsion technique as described by Dziubla, et al, 2005, cited above. Using concepts of amphiphile self-assembly, the inventors hypothesized that the copolymer block ratio that controls spontaneous curvature would influence PNC morphology and loading and examined PNC yield, shape, stability, loading, activity and protease resistance of the exemplary antioxidant enzyme, catalase. It was surprisingly discovered that PNC transitioned from spherical to filamentous shapes with increasing hydrophobic polymer fraction. Importantly, the inventors demonstrated for the first time encapsulation of an active therapeutic enzyme into filamentous carriers. As noted in the examples below, a PNC produced as described herein using a diblock copolymer formed filamentous particles loaded with significant levels of protease-resistant enzyme. The inventors further determined that PNC morphology also greatly influenced its degradation, offering a new means of controlled delivery.

The methods described herein use varying polymer MW and amphiphilicity in the freeze thaw synthesis of PNC to develop desirable PNC compositions loaded with protein. With constant hydrophilic polymer block (e.g., PEG) content, the MW of the hydrophobic polymer block (e.g., PLA) in the diblock copolymer determines the overall amphiphilicity.

Thus, in such a method the primary emulsion is formed using a freeze-thaw cycle of an amphiphilic diblock copolymer, which has a molecular weight of about 10,000 to about 100,000 Da and comprises a conjugate of the hydrophobic polymer block and a hydrophilic polymer block, and a protein having a molecular weight of up to or equal to 300,000 Da.

The method includes forming the emulsion by mixing or homogenizing the amphiphilic diblock copolymer with aqueous solutions of the protein by methods including, but not limited to, mechanical or ultrasound homogenization or pressure homogenization. A secondary emulsion is formed generally by mixing or homogenizing the primary emulsion with a surfactant. The nanoparticles having the requisite physical characteristics are recovered therefrom, generally following one or more centrifugations.

In one embodiment, when a weight percentage of hydrophobic polymer block in a total amphiphilic diblock copolymer of the primary emulsion is about 60% to less than 80% by weight of the hydrophobic polymer block in this method, polymeric nanocarrier-encapsulated protein particles are produced having a substantially or primarily spherical shape. The method produces spherical nanoparticles having diameters of about 250 to 350 nm. Thus, in certain embodiments, the spherical nanoparticles produced by this method have a diameter of at least 250, 260, 270, 280, 290, 300, 310, 320, 330, 340 or 350 nm.

In another embodiment, when a weight percentage of hydrophobic polymer block in a total amphiphilic diblock copolymer of the primary emulsion is from 80% to less than 81% by weight of the hydrophobic polymer block, the polymeric nanocarrier-encapsulated protein particles are produced having a mixture of spherical and filamentous shapes.

In yet another embodiment, a method of producing filamentous polymeric nanocarrier-encapsulated protein particles is disclosed herein. According to this method, a primary emulsion is formed using a freeze-thaw cycle of an amphiphilic diblock copolymer, which has a molecular weight of about 10,000 to about 100,000 Da and comprises a conjugate of the hydrophobic polymer block and a hydrophilic polymer block, wherein the amphiphilic diblock copolymer comprises greater than 81% to about 95% by weight of the hydrophobic polymer block; and a protein having a molecular weight of up to or equal to about 300,000 Da. A secondary emulsion is formed from the primary emulsion. The method also includes recovering polymeric nanocarrier-encapsulated protein particles having a primarily filamentous shape from this method. Filamentous nanoparticles produced by this method have a diameter of less than 70 nm. In one embodiment, such filamentous particles have a diameter of 30-60 nm, dependent on the copolymer MW. In other embodiments, the particles have a diameter of at least 60 nm, 50 nm, 40 nm, 30 nm or lower. Such filamentous nanoparticles also have a length of from about 1 to about 50 microns. Thus, in certain embodiments, the filamentous nanoparticles produced herein have lengths of at least 2, 5, 10, 15, 20, 25, 30, 35, 40, 45 or 50 microns in length.

All of the methods described above may further include an additional method step of conjugating an affinity moiety to the surface of the polymeric nanocarrier-encapsulated protein particles.

Thus, in another aspect, a composition is provided that comprises polymeric nanocarrier-encapsulated protein particles comprising (a) a protein having a molecular weight of up to or equal to about 300,000 Da; (b) an amphiphilic diblock copolymer having a molecular weight of about 10,000 to about 100,000 Da and comprising a conjugate of a hydrophilic polymer block and a hydrophobic polymer block, wherein the total amphiphilic diblock copolymer comprises greater than about 80% by weight of the hydrophobic polymer block. This composition comprises filamentous-shaped nanocarrier particles. In one embodiment of this composition in which the total amphiphilic diblock copolymer comprises between 80-81% by weight of the hydrophobic polymer block, the composition comprises a mixture of spherical shaped particles and filamentous particles. In another embodiment of this composition in which the total amphiphilic diblock copolymer comprises between 82 to 95% by weight of the hydrophobic polymer block, the composition comprises primarily filamentous particles.

These compositions containing filamentous particle have particular utility in drug delivery. For instance, other non-spherical, oblong particles can be phagocytosed (Champion, J. A.; Mitragotri, S., *Proc Natl Acad Sci USA* 2006, 103, (13), 4930-4) and useful for controlled delivery (Son, S. J. et al, *J Control Release* 2006, 114, (2), 143-52). The unique filamentous morphology of compositions described herein offers several advantageous features. For instance, the relatively extensive length translates into a high potential volume for drug cargo loading while the small cross section retains the carrier's nano status. Other filamentous nanostructures have shown the potential for unprecedented extended circulation (likely due to alignment with flow), allowing a novel extended release depot delivery system (Cai, S. et al, *Pharm Res* 2007 24, 2099-2109; Geng et al, *Nat. Nano* 2007, 2(4):249-255; Geng, et al, *Polymer* 2006, 47(7): 2519-2525).

Another composition described herein comprises polymeric nanocarrier-encapsulated protein particles comprising (a) a therapeutic protein having a molecular weight of up to or equal to 300,000 Da; and (b) an amphiphilic diblock copolymer having a molecular weight of about 10,000 to about 100,000 Da and comprising a conjugate of a hydrophilic polymer block and a hydrophobic polymer block, wherein the total amphiphilic diblock copolymer comprises about 60 to 80% by weight of the hydrophobic polymer block. This composition comprises spherical particles with diameters of about 250 to 350 nm.

These compositions are produced by a double emulsion formulation without inactivation of the encapsulated protein, wherein the size and shape of the protein composition and protection of the protein against external proteolysis and mechanism of degradation of the nanocarriers are controlled by the weight percentage of the hydrophobic polymer block in the total amphiphilic diblock copolymer. These compositions prolong enzymatic activity and protect enzymatic activity from premature deactivation.

The components of the above described methods and compositions are described in detail below.

In certain embodiments, an amphiphilic diblock copolymer comprising a hydrophobic block polymer and a hydrophilic block polymer, useful in these methods and compositions has a molecular weight of between about 10,000 to about 100,000 Da. In one embodiment, such an amphiphilic diblock copolymer has a molecular weight of about 10,000 to about 40,000 Da. In certain other embodiments, the amphiphilic diblock copolymer has a molecular weight of at least 10,000 Da, 20,000 Da, 30,000 Da, 40,000 Da, 50,000 Da, 60,000 Da, 70,000 Da, 80,000 Da, 90,000 Da, up to 100,000 Da. The amphiphilic diblock copolymer is also permeable to substrates of the encapsulated protein, which is discussed below. In other embodiments, the diblock copolymer may be replaced with an amphiphilic triblock or multi-block copolymer.

The hydrophobic and hydrophilic block copolymers useful in the methods and compositions herein are desirably composed of a polymeric-backbone having functional (e.g., pendant side chain or endcapped) groups for physically cross-linking with other entities, including affinity moieties, therapeutic entities, or other polymers. Functional groups encompass conjugatable groups such as amines, hydroxyls, carbonyls, thiols, and carboxylic acids for covalently bonding of other bioactive molecules to the surface of the polymeric nanocarrier. The linkages formed following conjugation of the bioactive molecules to the conjugatable groups include amides, esters, and thioethers, among others.

A suitable hydrophobic polymer block of the amphiphilic diblock copolymer includes, without limitation, a poly(lactic acid) polymer, a polymer having amphiphilicity similar to that of a poly(lactic acid) polymer, such as a polycaprolactone polymer, a polyglycolic acid and their associated copolymers, e.g., poly(lactide-co-glycolide) at all lactide to glycolide ratios, and both L-lactide or D,L-lactide. In particular embodiments, a polylactic acid (PLA) is employed.

A suitable hydrophilic polymer block includes, without limitation, polypyrrolidone, poly(amino acids), polyether, polysaccharide or polyacrylic acid and its hydrophilic ester derivatives; and hydrophobic blocks, e.g., polyanhydrides, polydioxanones, polyphosphazenes, polyesters, polylactones, polyfumarates, polymers of alpha-hydroxy carboxylic acids, polyhydroxybutyric acid, polyorthoesters, polycaprolactone, polyphosphates, or copolymers prepared from the monomers of these polymers. In one embodiment the hydrophilic polymer block of the amphiphilic diblock copolymer is a modified or unmodified polyethylene glycol. The modified polyethylene glycol is selected from the group consisting of methoxypolyethylene glycol, amine modified polyethylene glycol, biotinylated polyethylene glycol, and an alkyne terminated polyethylene glycol. Generally PEG polymers for use herein have a molecular weight of from about 1000 to about 7500 Da, or more suitably with molecular weights of from about 3000 to about 6000 Da. In certain embodiments, the hydrophilic domain of the block copolymer has a molecular weight in the range of 100 to 20000 Da. In one embodiment, the hydrophilic block of the copolymer exists as an ester end-capped form. In another embodiment, the hydrophilic block of the copolymer exists in its native form providing linkage sites for an affinity moiety.

The ratio of the hydrophobic block polymer molecular weight to the total diblock copolymer molecular weight may be calculated as described in the examples below. Number average molecular weights ($\overline{M_n}$) of bulk copolymers are determined using a conventional technique, such as proton nuclear magnetic resonance. The weight average molecular weights ($\overline{M_w}$) and polydispersity indices (PDI) are determined by gel permeation chromatography. The ratio of the hydrophobic block copolymer MW to the total diblock MW is defined as the wt % of the hydrophobic block copolymer. The polydispersity indices (PDI) of the polymers are defined by the formula $\overline{M_w}/\overline{M_n}$, and determined using GPC.

As noted above, for the amphiphilic diblock copolymers to operate in the methods defined herein and produce the desired nanocarrier particle morphology the above noted ratio, or weight percentage of the hydrophobic copolymer block is equal to or greater than about 81% to produce a filamentous shaped particle, or between 80-81% to produce a mixture of spherical and filamentous particles, and less than 80% to produce spherical particles.

In an embodiment provided by the examples below, the amphiphilic diblock copolymer of the methods and compositions has a polyethylene glycol (PEG) as its hydrophilic block and a polylactic acid polymer (PLA) as its hydrophilic block.

In all of the above polymeric nanocarriers (PNCs) produced by these methods, the encapsulated protein or mixture of two or more proteins, is not inactivated.

A protein, as used in the context of the present invention, includes without limitation, structural proteins such as albumins, globulins, histones, collagens, elastins, and keratins; and proteins with a chemical function to fulfill, e.g., enzymes, protein molecules united with nonprotein molecules to produce compound proteins such as nucleoproteins, mucoproteins, lipoproteins and metalloproteins. A protein useful in the methods and compositions herein is naturally-occurring, synthetic or semi-synthetic.

In one embodiment, the protein is suitable for therapeutic or diagnostic use. Functionally active proteins that are particularly useful for encapsulation in the instant polymeric nanocarrier include clinically relevant proteases and their inhibitors such as serpins, growth factors and hormones, enzymes, e.g., anticoagulants and fibrinolytic plasminogen activators, interferons and cytokines, antibodies, antibody fragments and their conjugates with toxins and other biologically active agents. Among useful enzymes for encapsulation in the PNCs described herein are an antioxidant enzyme which is capable of reducing oxidative damage by decomposing or degrading reactive oxygen species. Antioxidant enzymes particularly useful include, without limitation, catalase, glutathione peroxidase, superoxide dismutase, hemeoxygenase, glutathione-S-transferase, or synthetic or mimetic enzymes thereof.

In another embodiment, the encapsulated protein is an enzyme that detoxifies a xenobiotic such as insecticides, drugs, pharmaceutical agents, organic chemicals, chemical warfare agents, toxins (including endotoxins), and the like which can have an adverse effect on a subject. Xenobiotic detoxifying enzymes particularly suitable for encapsulation in the instant polymeric nanocarrier include, but are not limited to, cytochrome P450 enzymes such as Cyp3A4 and Cyp3A5, Cypl A1, CyplA2, Cyp2D6, Cyp2E1, Cyp2C, Cyp2C9, Cyp2B6, Cyp2C19 and the like which are responsible for the metabolism of a variety of drugs including cyclosporin, nifedipine, warfarin, phenacetin, caffeine, aflatoxin B1, ethanol, carbon tetrachloride, coumarin, sparteine, cyclophosfamide. Suitable enzymes further include alcohol dehydrogenase; epoxide hydrolase; glucuronyl transferases (detoxifying phenols, thiols, amines, and carboxylic acids); sulfotransferase (detoxifying phenols, thiols, and amines); N- and O-methyl transferases (detoxifying phenols and amines); N-acetyl transferase (detoxifying amines); and other peroxisomal enzymes including peroxidases, catalase, phytanoyl-CoA hydroxylase, and α-methylacyl-CoA racemase. In cases where the xenobiotic is of an unknown origin, it is contemplated that a polymeric nanoparticle containing a plurality of detoxifying enzymes can be employed to facilitate detoxification of the unknown agent.

Still other enzymes that are suitable for encapsulation in the PNC described herein are useful in diagnostic applications and are referred to generically as reporter enzymes. Such suitable enzymes include, without limitation, horseradish peroxidase, xanthine oxidase, Protein C, Superoxide Dismutase, NADPH oxidase, P450 oxidases, β-glucouronidase, luciferase, β-galactosidase, as well as other known enzymes conventionally employed in diagnostic assays. Additional such enzymes may be identified in standard texts and in catologs of pharmaceutical and diagnostic reagents.

Substrates of the encapsulated protein to which the amphiphilic block copolymer is permeable include, well-known substrates of the specific enzymes selected, i.e., those proteins on which the enzymes acts. For example, suitable substrates of the encapsulated protein to which the amphiphilic block copolymer is permeable include, without limitation, hydrogen peroxide, o-phenylenediamine, hypoxanthine, cytochrome P450 enzyme substrates including 7-benzyloxy-4-trifluoromethylcoumarin, 7-ethoxycoumarin, 7-methosy-5-trifluoromethylcoumaring, 7-benzyloxyquinoline, or 7-benzyloxy-4-trifluyoromethylcoumarin; epoxy hydrolase enzyme substrates such as 2S,3S)-trans-3-Phenyl-2-oxiranylmethyl 4-nitrophenyl carbonate; methyl transferase enzyme substrates such as N-Acetyl-S-geranylgeranyl-L-cysteine; peroxidase enzyme substrates such as N-(4-Aminobutyl)-N-ethylisoluminol, 3-(4-Hydroxyphenyl) propionic acid, 2,2'-Azino-bis(3-ethylbenzothiazoline-6-sulfonic acid) diammonium salt, 3-Amino-9-ethylcarbazole, 4-Aminophthalhydrazide monohydrate, 3-Amino-9-ethylcarbazole, 4-Aminoantipyrine, 5-Aminosalicylic acid, 2,2'-Azino-bis(3-ethylbenzothiazoline-6-sulfonic acid), 4-Chloro-1-naphthol, 4-Chloro-7-nitrobenzofurazan, 3,3'-Diaminobenzidine, o-Dianisidine dihydrochloride, Dicarboxidine dihydrochloride, Sodium 3,5-dichloro-2-hydroxybenzenesulfonate, Dihydrorhodamine, o-Dianisidine dihydrochloride, 3-(Dimethylamino)benzoic acid, Guaiacol, Iodonitrotetrazolium chloride, Neotetrazolium chloride, o-Phenylenediamine, o-Phenylenediamine dihydrochloride, Pyrogallol, 3,3'-Diaminobenzidine, Tetramethylbenzidine dihydrochloride, Tetramethylbenzidine, and hydrogen peroxide. Other enzyme substrates are hereby incorporated by reference from the reagents catalog available from Sigma Aldrich (St. Louis, Mo.).

For use in both the methods and compositions described herein an affinity moiety may be used to modify the outer surface of the polymeric nanocarrier-encapsulated protein particle. An affinity moiety refers to any material or substance which can promote targeting of the PNC compositions described herein to particular cells, tissues and/or receptors in vivo or in vitro. The affinity moiety can be synthetic, semi-synthetic, or naturally-occurring. Exemplary affinity moieties include, without limitation, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, bioactive agents, and genetic material, including nucleosides, nucleotides, nucleotide acid constructs, oligonucleotide aptamers, and polynucleotides. Particularly suitable affinity moieties include molecules which specifically bind to receptors or antigens found on vascular cells. Other suitable affinity moieties target endothelial receptors, tissues or other targets accessible through a body fluid or receptors or other targets upregulated in a tissue or cell adjacent to or in a bodily fluid. For example, affinity moieties attached to nanocarriers designed to deliver proteins to the eye can be injected into the vitreous, choroid, or sclera; affinity moieties attached to nanocarriers designed to deliver proteins to the joint can be injected into the synovial fluid; or affinity moieties to the spine and brain can be delivered into the cerebral spinal fluid.

The affinity moiety can have other effects, including therapeutic effects, in addition to specifically binding to a target. For example, the affinity moiety can modulate the function of an enzyme target. By modulating cellular function, the affinity moiety is meant to alter/enhance cellular response when compared to not adding the affinity moiety. In most cases, a desired form of modulation of function is inhibition. Examples of affinity moieties which can have other functions or effects include agents such as Combrestastatin A4 Prodrug (CA4P) which can be used as a vascular affinity moiety that also acts as an anti-angiogenesis agent; and Cidecin, a cyclic lipopeptide, used as a bactericidal and anti-inflammatory agent.

Exemplary affinity moieties attached to the polymeric nanocarrier described herein include, but are not limited to, an antibody or fragment thereof which binds a selected cell surface receptor. An exemplary cell surface receptor is a cell adhesion molecule, such as, platelet-endothelial cell adhesion molecule (PECAM-1) or inter-cellular adhesion molecule (ICAM-1). Other affinity moieties include peptides such as RGD-containing peptides (see, e.g. U.S. Pat. No. 5,866,540); bombesin or gastrin-releasing peptide; and peptides designed de novo to be complementary to tumor-expressed receptors, antigenic determinants, or other receptor targeting groups. These affinity moieties can be used to control the biodistribution, non-specific adhesion, and blood pool half-life of the polymeric nanocarrier compositions.

In particular embodiments, the affinity moiety is attached by covalent means. In another embodiment, the attachment is by non-covalent means. For example, antibody affinity moieties can be attached by a biotin-avidin biotinylated antibody sandwich to allow a variety of commercially available biotinylated antibodies to be used on the coated polymeric nanocarrier. In other embodiments, the affinity moiety is added in a single step, e.g., through the coupling of biotinylated nanocarriers and antibody-streptavidin chemical conjugate or fusion construct.

Figure 6:
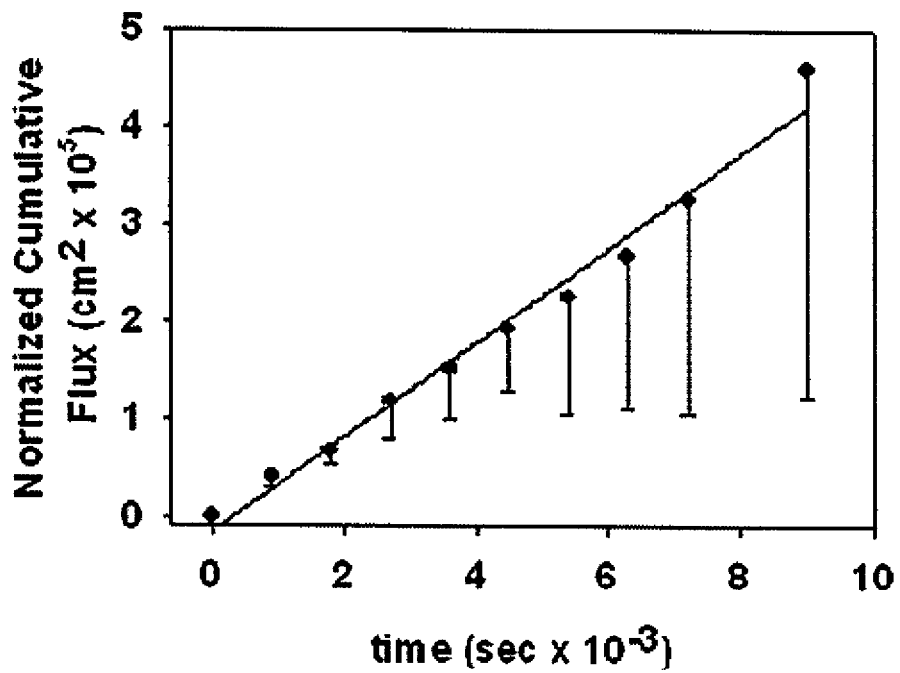
FIG. 6 is a graph showing the diffusivity, or permeability coefficient, D, of catalase enzyme loaded nanocarriers as the slope of the flux curve.

The compositions described herein may be adapted for use in diagnostic or therapeutic methods, depending upon the identity of the encapsulated protein. Polymeric nanocarrier compositions described herein can be administered to any animal, desirably to mammals, and more desirably to humans. The composition described above, or prepared as described above, are anticipated to be stable when administered in vivo to a human subject, based upon the in vitro stability data illustrated in FIGS. 4A-4D. Photomicrographs showing pH influenced degradation of filamentous PNC were also taken, not shown here, but reproduced in Simone et al, 2007 Biomacromolecules, 8(12):3914-3921 as FIG. 6. These photomicrographs show degradation at pH 7.4 and pH 2.5, respectively, on Day 0; degradation at pH 7.4 and pH 2.5, respectively, on Day 7; degradation at pH 7.4 and pH 2.5, respectively, on Day 14; and degradation at pH 7.4 and pH 2.5, respectively, on Day 21. Morphology changes of (87% PLA) filamentous PNC by TEM over 1 month degradation in neutral and acidic pH are shown. Filamentous PNC show higher sensitivity at pH 2.5, while no morphologic change is evident at neutral pH. Similar trends for filamentous PNC composed of PEG copolymer with higher PLA MW were observed.

In one embodiment, therefore, a PNC as described herein containing a therapeutically active protein is administered to a subject or tissue thereof in vivo or ex vivo for treatment of a disease responsive to the presence of that protein. In one embodiment, these compositions are useful when administered ex vivo for organ transplantation. Exemplary diseases or conditions requiring therapeutic intervention include, without limitation, oxidative stress, atherosclerosis, stroke, hypertension, inflammation, acute Lung Injury (ALI/ARDS), thrombosis, ischemia-reperfusion injury, organ transplantation, diabetes, angina and myocardial infarction.

An antioxidant enzyme encapsulated in the instant polymeric nanocarrier is particularly useful in methods for detoxifying reactive oxygen species including the superoxide anion radical ($O_2$), hydrogen peroxide ($H_2O_2$), hypochlorous acid (HOCl), hydroxyl radical (OH.), and singlet oxygen ($^1O_2$) which are generated in the body, mediating cell damage and apoptosis.

When the instant polymeric nanocarrier contains an antioxidant enzyme and an affinity moiety for targeting vascular endothelial cells, sustained therapy against vascular oxidative stress can be achieved for the prevention or treatment of pathological processes involved in disease conditions including atherosclerosis, hypertension, diabetes, stroke, myocardial infarction, acute lung injury, inflammation and ischemia-reperfusion injury. Administration of the nanocarrier-encapsulated antioxidant enzyme can be as in intervention in debilitating situations such as acute lung injury, sepsis (toxic shock), autoimmune diseases, etc., thereby limiting the progressive damage caused by ROS under these extreme oxidative stress situations.

When the instant polymeric nanocarrier contains an enzyme which detoxifies xenobiotics, the PNC can be used to reduce, inhibit, or ameliorate the effects of an intentional or unintentional exposure (including overdosing) to one or more xenobiotics. Moreover, compositions described herein can provide detoxifying enzymes to subjects with impaired liver function, e.g., due to alcoholism, fatty liver disease, biliary cirrhosis, and hepatocarinomas leading to lower detoxification activity in general, or suffering from a peroxisomal disorder such as hyperoxaluria, Refsum disease, and β-oxidation disorders.

In another embodiment, a PNC as described herein containing a reporter protein is administered in vitro to a cell culture or tissue culture for diagnostic or research purposes, as well as administered in vivo for diagnostic purposes. Such diagnostic methods may include detection of cancerous cells in tissue sections or explants or cell cultures or detection of any abnormal cell receptor when the PNC contains an affinity moiety capable of targeting that receptor or cell.

Administration of these compositions may include, without limitation, the following routes: intravenous, intranasal, topical, sublingual, ocular, buccal, parenteral, interperitoneal, intrathecal, subcutaneous, topical, oral, by aerosol, or local administration, into the vasculature, lungs, lymphatic system, synovial fluid, ocular fluid, or spinal fluid or other body tissues.

Differing administration vehicles, dosages, and routes of administration can be determined for optimal administration of the instant nanocarrier compositions; for example, injection near the site of an injury or tumor may be preferable for facilitating local treatment. For example, biodegradable nanocarriers encapsulating an anti-inflammatory (e.g., hydrocortisone) and growth factors (e.g., BDNF) can be administered via direct lumbar injection using a standard spinal tap procedure. Nanocarriers introduced into the cerebral spinal fluid are dispersed through this space via natural convective motion and accumulate at the wound site as a result of the enhanced permeation and retention (EPR) effect. Also, targeting can be further enhanced by the inclusion antibodies toward common inflammatory markers.

Generally, the nanocarrier compositions used in the invention are administered to an animal in an effective amount, which is defined as an amount of encapsulated protein effective to either reduce the symptoms of the disease sought to be treated or induce a pharmacological change relevant to treating the disease sought to be treated. Therapeutically effective amounts of the encapsulated proteins can be any amount or doses sufficient to bring about the desired effect and depend, in part, on the condition, type and location of the pathology, the size and condition of the patient, as well as other factors readily known to those skilled in the art. The dosages can be given as a single dose, or as several doses, for example, divided over the course of several weeks.

Depending upon the mode of administration and the condition being treated or diagnosed, a polymeric nanocarrier composition of the instant invention can be formulated with an excipient. See, e.g., Remington: The Science and Practice of Pharmacy, Alfonso R. Gennaro, editor, 20th ed. Lippincott Williams & Wilkins: Philadelphia, Pa., 2000. As described in the examples below, the inventors prepared PNC composed of a series of diblocks combining a 5,000 MW hydrophilic polymer (e.g., PEG) block with hydrophilic polymer (e.g., PLA) blocks of diverse molecular sizes. Of note, these PNC are not typical self-assembled particles formed from solvent-free amphiphiles that have been re-hydrated with water. Rather, a more complex structure occurs with the present PNC that result from the freeze thaw double emulsion formulation. A schematic of freeze thaw-emulsion formulated polymeric nanocarriers (PNC) showing that PNC yield and effective size depend on the molecular weight percentage of the hydrophobic block polymer (e.g., polylactic acid) in the amphiphilic diblock copolymer (also containing a hydrophilic block polymer) can be seen in FIG. 1 of Simone et al, 2007 cited above.

Based on PNC yield and enzyme loading data, copolymers containing 63-84% PLA have sufficient amphiphilicity for formulation of PNC with effective diameters on the order of 500 nm or less, and significant catalase activity that is markedly protected against external proteolysis. PNC in the sub-500 nm range are readily internalized when targeted to appropriate cell surface receptors and thus are useful candidates for intracellular delivery. Lower PLA content provided no significant PNC yield. The encapsulated enzyme, catalase, inactivation was more profound in more hydrophobic polymers (93% and 100% PLA). The enhanced hydrophobicity of these PNC translates into stronger protein-surface interactions and adsorption that may interfere with the enzyme's activity (Shuvaev, V. V. et al, *J Control Release* 2007, 118, (2), 235-44).

Double emulsion formulations typically produce PNC with both encapsulated and surface adsorbed protein loads. Polymer amphiphilicity appears to control this ratio. Surface adsorbed protein is not protected against proteolysis, as appears to be the case for less amphiphilic, and thus more hydrophobic, 93% PLA PNC. However, filamentous 84% PLA PNC provided protection of encapsulated catalase comparable to that of spherical 78% PLA PNC. This notion of surface adsorption versus encapsulation coincides with the observed enzyme protection from proteolysis for the spherical PNC observed in the 80% PLA range, as has been proven with this system for a similar PEG PNC that was ~80% PL(G)A. It is unlikely that degradation of the polymer itself would contribute to enzyme inactivation. There is no detectable change in either polymer MW by GPC (data not shown) or PNC number over the course of 1 day, the timeframe within which catalase activity studies were performed. Further, cross sectional diameters of 93% PLA filamentous PNC are much smaller than those observed for 84% PLA filamentous PNC (35.4±5.3 nm vs. 68.3±7.3 nm, respectively).

From a geometric standpoint, the 93% PLA filamentous PNC possessed only 26% of the internal volume per unit length afforded to the 84% filamentous PNC, suggesting that the degree of encapsulation may be dependent upon filament diameter. In other words, the ratio of encapsulated to surface-adsorbed catalase is expected to be lower in 93%, relative to 84%, PLA filamentous PNC, explaining the loss of protease resistance observed in the former formulation.

The PLA MW also controlled shape and degradation of the formed PNC. In the case of spherical PNC, a decrease in PNC number with stable mean diameter is characteristic of bulk erosion and homogeneous degradation of particles: the nominal diameter remains stable until the PNC erodes throughout to a burst point, diminishing the net number of PNC. This coincides with degradation properties observed with polyester PLA and PLGA nano-structures (von Burkersroda, F. et al, *Biomaterials* 2002, 23, (21), 4221-31; Gopferich, A., *Macromolecules* 1997, 30, (9), 2598-2604). Lowering the pH and polymer MW accelerates the PNC degradation, most likely due to accelerated polymer hydrolysis.

Conversely, the gradual decrease in effective diameter and corresponding increase in number of particles (FIGS. 4C and 4D), unexpected for homogeneously degrading nanoscale polyester structures, are suggestive of an alternative mechanism of degradation of filamentous PNC. Filamentous PNC fragment into shorter filaments and eventually spheres. Thus, this form of degradation serves as a depot of spherical, more diffusible carriers. Similar to spherical PNC, lowering the pH and polymer MW accelerated degradation of the filamentous PNC (data not shown). This raises an interesting point regarding DLS analysis of non-spherical particles. Light scattering is proportional to both the particle area and the number of particles. As the filamentous structures fragment and become spherical, the diffusion rate increases (resulting in a smaller hydrodynamic radius), but the average cross-sectional area of the light path increases, leading to an increase in scattering. Therefore, the obtained data reflect an increase in the number of particles. Disruption of filamentous PNC by ultrasound led to increased scattering intensity that reflected an increased number of PNC fragments.

As demonstrated herein, polymer MW can be employed to control physical properties of active enzyme-loaded filamentous PNC. In particular, stiffness, length, and cross sectional diameter can be finely tuned through alterations in the absolute polymer MW. Due to the unique thermal properties of the polymers utilized for carrier formation, the resultant filamentous f-PNC are quite flexible at physiologic temperatures. Furthermore, control of the polymer backbone structure enables protein-loadable filaments across a broad range of polymer MWs. This offers a new genre of non-spherical enzyme delivery devices, with several potential applications both in targeting and sub-cellular addressing.

Particles of anisotropic geometry, such as filamentous or even disk-shaped carriers have several unique features as drug delivery systems. Despite the nano cross sectional diameters of many of these carriers, namely filaments, their micron scale lengths afford them a tremendous drug loading capacity. In particular, these very same dimensional attributes, combined with varying degrees of flexibility, enable unprecedented, prolonged circulation residence times in some animal models and provide unique paradigms in terms of sub-cellular addressing. Similarly, the fact that these carriers are essentially all surface makes them ideal candidates for drug targeting, where site-specific epitopes would be conjugated to their surface. Therapeutic cargoes could also be loaded via the same mechanism.

These examples for the first time demonstrated simultaneous encapsulation and protection of an active enzyme within filamentous PNC. All chemicals and reagents used in the examples below were purchased from Sigma-Aldrich (St Louis, Mo.) and used as received unless otherwise stated. As illustrated in the examples below, various PLA molecular weights (MW's), and consequently block copolymer MW ratios, were investigated in terms of resultant PNC morphology, enzyme loading and cargo protection from proteolytic degradation.

EXAMPLE 1

Synthesis of Diblock Copolymers

DL-lactide was re-crystallized twice in anhydrous ether, before mixing with methoxy poly(ethylene glycol) (mPEG)

MW 5,000 (Polysciences, Warrington, Pa.) in stoichiometric ratios to achieve desired molecular weights. Reactants were heated to 140° C. under nitrogen while stirring for 2 hours to remove trace water from samples. The temperature was reduced to 120° C. and stannous octoate (1 wt %) was added to catalyze the ring opening polymerization (ROP) of lactide with mPEG as the initiator. The polymerization was allowed to continue for 6 hours. The diblock copolymer was then dissolved in dichloromethane (DCM) and twice precipitated in cold diethyl ether. Residual solvent was then removed by first drying via rotary evaporation (SAFETY VAP® 205 system, Buchi, Switzerland), followed by lyophilization (RCT 60, Jouan, Winchester, Va.).

Number average molecular weights ($\overline{M_n}$) of bulk copolymers were determined using proton nuclear magnetic resonance ($^1$H-NMR). The weight average molecular weights ($\overline{M_w}$) and polydispersity indices (PDI) were also determined by gel permeation chromatography (HPLC-GPC), with a Binary HPLC pump (1525, Waters, Milford, Mass.), a Refractive Index Detector (2414, Waters) and three serial 7.8×300 mm STYRAGEL® columns (Waters) using tetrahydrofuran (THF) as the mobile phase. Chromatograms were analyzed using Breeze version 3.3 software with polystyrene standards used for calibration.

Table 1 reports data for synthesized polymer characterization. Number and weight average molecular weights are indicated by the symbols ($\overline{M_n}$ and $\overline{M_w}$ respectively). The resultant wt % PLA, or "% PLA", defined as the ratio of PLA MW to the total diblock MW, is also shown in Table 1. The polydispersity indices (PDI) of the polymers are defined by the formula $\overline{M_w}/\overline{M_n}$ and determined using GPC. Actual % PLA, or wt % PLA, is defined as the ratio of the actual PLA block $\overline{M_n}$ to the entire diblock copolymer $\overline{M_n}$.

By controlling reaction feed ratios, ring-opening polymerization (ROP) of lactide with a monomethoxy-capped mPEG initiator yielded mPEG-PLA with PLA block MW's from 800 Da to 64,000 Da as determined by $^1$H-NMR. All diblocks contain a methoxy end-capped 5,000 MW mPEG, which served as the initiator for the ring opening polymerization (ROP) of lactide into PLA. As noted in the Table 1, PDI slightly increased with increasing MW, from 1.1 for smaller PLA polymers to 1.8 for the largest ones, as expected for ROP products.

TABLE 1

Enzyme in Filamentous and Spherical Polymer Nanocarriers Synthesized Polymer Characterization[a]

| Target PLA $M_n$ | PLA $M_n$[b] | % PLA | PLA $M_n$[c] | PLA $M_w$[c] | PDI |
|---|---|---|---|---|---|
| 1000.0 | 791.0 | 13.7 | 6032.8 | 6629.4 | 1.1 |
| 5000.0 | 2956.2 | 37.2 | 5666.2 | 6190.2 | 1.1 |
| 8000.0 | 6575.5 | 56.8 | 3898.9 | 7253.0 | 1.4 |
| 10000.0 | 8482.7 | 62.9 | 9974.1 | 11649.9 | 1.1 |
| 20000.0 | 18226.7 | 78.5 | 23236.7 | 36908.2 | 1.5 |
| 25000.0 | 21252.7 | 81.0 | 21497.8 | 34530.8 | 1.5 |
| 30000.0 | 27091.3 | 84.4 | 21859.0 | 35792.4 | 1.5 |
| 35000.0 | 34557.6 | 87.4 | 21079.4 | 39442.7 | 1.7 |
| 65000.0 | 64330.2 | 92.8 | 19169.4 | 37650.1 | 1.8 |

[a]indicates that the measurement was determined by $^1$H-NMR
[b]indicates that the measurement was determined by GPC.

The formulation scheme utilized throughout these studies for nanocarrier synthesis and protein encapsulation, and the resultant morphology is described herein and illustrated in Simone et al, 2007 cited above as FIG. 1.

EXAMPLE 2

Nanoparticle Formation

A freeze-thaw double emulsion solvent evaporation technique was used as previously described in Dziubla et al 2005 cited above and US Patent Application Publication No. 2006/0127386. Briefly, mPEG-PLA diblock copolymer is dissolved in DCM at 25 mg/ml. A 1 mg/ml bovine liver catalase (242 kDa) (Calbiochem, EMD Biosciences, San Diego, Calif.) solution and a polyvinyl alcohol (PVA) surfactant solution (2 wt %, 87-89% hydrolyzed, $\overline{M_w}$=13,000-23,000) in 20 mM PBS are prepared. The primary emulsion consisted of the organic phase (1 ml polymer—DCM mixture) and the aqueous phase (100 μl catalase solution) homogenized at 15 krpm for 1 minute in a dry ice-acetone bath with a 7 mm—blade homogenizer (KINEMETICA POLYTRON 3100 instrument with a PDTA3007/2 generator, Brinkmann Instruments, Westbury, N.Y.). The primary emulsion was then added to 5 ml of the PVA surfactant solution and homogenized at 15 krpm for 1 minute. The resultant mixture was added to 10 ml of PVA solution and stirred overnight to allow removal of the residual solvent. The microparticle fraction was removed by a primary centrifugation at 1,000 g for 10 minutes. The nanoparticle fraction was collected by subsequent centrifugation at 20,000 g for 30 minutes. The supernatant was then removed and the PNC pellet was re-suspended in PBS and purified again by further centrifugation.

EXAMPLE 3

Enzyme Loading Determination

Protein loading was determined via radioisotope labeling and enzymatic activity. Loading via radiolabeling was determined as described before, by formulating PNC with $^{125}$I-labeled catalase following the directions of the above-referenced in Dziubla et al 2005 cited above. Catalase was radiolabeled with Na$^{125}$I (Perkin Elmer, Boston, Mass.) via the Iodogen method (Pierce Biotech., Rockford, Ill.). Unbound $^{125}$I was removed from catalase using BIOSPIN 6 columns in accordance with the manufacturer's instructions (Bio-Rad labs, Hercules, Calif.). Total solution $^{125}$I-catalase content was measured before centrifugation, and then radioactivity of the $^{125}$I-catalase/PNC-composed pellet after centrifugation was measured. A WIZARD 1470 gamma counter (Wallac, Oy, Turku, Finland) was used for radiotracing.

To determine loading via enzymatic activity, a catalase activity assay (Shuvaev, V. V. et al, *Methods Mol Biol* 2004, 283: 3-19) was used, both for the total sample before and after centrifugation. Briefly, 900 μl of 5 mM H$_2$O$_2$ in PBS and 100 μl of enzyme-loaded PNC was added to a quartz cuvette. The kinetics of H$_2$O$_2$ degradation was then measured with a spectrophotometer at 242 nm (absorbance at this wavelength corresponds to the H$_2$O$_2$ concentration; 1 Unit=23, ΔAbs/ml).

EXAMPLE 4

Catalase Protection Against Proteolysis

Protection against proteolysis was tested as described previously in Dziubla et al 2005 cited above. Briefly, PNC preps loaded with $^{125}$I-catalase were incubated with a 0.2 wt % protease (pronase) solution at 37° C. in a shaker bath set at 60 rpm for 1 hour. Samples were removed and centrifuged at 16,000 g for 20 minutes. Supernatant containing degraded protein and pellet containing intact protein encapsulated within PNC were collected and counted.

EXAMPLE 5

In vitro Degradation of PNC

Solutions of neutral physiologic (pH 7.4) PBS, moderately acidic lysosomal—mimetic (pH 5.0) MES, and strongly acidic (pH 2.5) sodium citrate were prepared. A buffer concentration of 150 mM was selected for these solutions to ensure that the buffering capacity would not be saturated during polymer degradation and lactic acid accumulation. Based upon the Henderson-Hasselbach equation, complete degradation of $PNC_{65kDa}$ polymer would result in a maximum pH change of 0.011. PNC formulations were incubated in these buffer solutions in a shaker bath at 37° C., shaking at 60 rpm to minimize sedimentation (50-Reciprocating Shaker Bath, Precision—Jouan, Inc., Winchester, Va.). Samples for transmission electron microscopy (TEM), GPC and lactic acid content assays were taken weekly over the 28-day duration of the study.

EXAMPLE 6

PNC Size Determination

Aliquots of 20 µl (for PNC size measurements) collected at the onset of the study and every 3 days afterwards were placed in NMR tubes and diluted with 200 µl of the appropriate pH buffer in triplicate. Size and relative number of PNC, proportional to measured scattering intensity, were determined via dynamic light scattering (DLS, 90PLUS Particle Sizer, Brookhaven Instruments, Holtsville, N.Y.). When a classical scattering expression for PNC is adapted, it is evident that the average intensity of the scattered light is proportional to the actual number of scattering components present in the sample, i.e. $\langle I \rangle \propto N M^2 P(\theta)$, where N is the number of independent particles of size, M, and $P(\theta)$ is the sample scattering factor at scattering angle δ (Brown, J. C. et al, *Journal of Chemical Physics* 1975, 62, (3), 1136-44; Tanford, C., *Physical Chemistry of Macromolecules*. Wiley: New York, 1961; p 710). While there exist novel methods for counting the precise number of nanoparticles (Epstein, H. et al, *Biomaterials* 2006, 27, (4), 651-9), the relative number as determined by scattering intensity is adequate for this study.

EXAMPLE 7

PNC Concentration Determination

PNC yield was determined via a colorimetric PEG assay based on the PEG-Barium Iodide complex. Prior to the assay, two solutions were prepared: solution A, consisting of 2.4 g of Barium chloride, 8.0 ml of 6 M HCl and 32 ml of deionized (DI) water, and solution B, consisting of 800 mg of potassium iodide, 500 mg of iodine, and 40 ml of deionized (DI) water. A 50 µl aliquot of PNC sample was hydrolyzed by adding 200 µA of 5 M NaOH and incubating overnight at 80° C. The pH of hydrolyzed PNC samples was then neutralized by addition of 5 M HCl and 20 µl aliquots were added to a multiwell plate and diluted to a 170 µl total volume with DI water. Subsequently, 40 µl of undiluted solution A and 1:5 diluted solution B were then added to each well. After a 10 minute incubation at room temperature, absorbance of the colored product was measured at 550 nm using the microplate reader (Sims, G. E.;

Snape, T. J., *Anal Biochem* 1980, 107(1), 60-3). Standard solutions of PEG (5,000 MW) were used for calibration.

For 100% PLA PNC, an enzymatic assay based on the detection of lactic acid monomer was used. Samples were hydrolyzed to their monomer state and neutralized as described above. Aliquots were similarly added to a multiwell plate. Then 50 µl of the assay buffer, consisting of 100 µl of 50 mU of lactate oxidase, 100 µl of 10 U ml$^{-1}$ of horseradish peroxidase (HRP; Calbiochem, EMD Biosciences, San Diego, Calif.), and 50 µl of 10 mM 10-Acetyl-3,7-dihydroxyphenoxazine (AMPLEX RED dye; Molecular Probes, Eugene, Oreg.) in dimethyl sulfoxide (DMSO), were added to each well. Lactate oxidase produces hydrogen peroxide in the presence of lactic acid, and the formed $H_2O_2$ is decomposed by HRP in the presence of AMPLEX RED dye, forming the fluorescent RESORUFIN product. After incubating for 10 min at ambient conditions the RESORUFIN concentration was determined by UV absorbance at 550 nm on a microplate reader (Model 2550-UV, Bio-Rad Labs, Hercules, Calif.). Pure lactic acid solutions were used for calibration.

EXAMPLE 8

PNC Morphology Study

PNC morphology was determined by fluorescence microscopy and transmission electron microscopy (TEM). For fluorescence microscopy, aliquots of PNC were stained with the lipophilic carbocyanine dye, PKH26, via established methods (Dalhaimer, P. et al, *Macromolecules* 2003, 36, (18), 6873-6877) and then imaged with a Nikon confocal microscope equipped with a 60× oil immersion objective. For electron microscopy, 5 µl of each sample were applied to a separate TEM mesh grid (FORMVAR FILM 200 Mesh, Electron Microscopy Sciences, Hatfield, Pa.) and excess was removed before drying. Samples were stained with filtered (0.1 µm filter) 2 wt % uranyl acetate (UA; Electron Microscopy Sciences, Fort Washington, Pa.) for 5 minutes in the dark and then washed with filtered DI water. Grids were dried at ambient conditions for 1 hour before they were imaged on a JEOL JEM-100CX TEM.

EXAMPLE 9

PLA Content in PLA-PEG Diblock Controls PNC Yield and Morphology

PLA MW influenced yield and morphology of PNC formulated by the freeze thaw emulsification process (FIGS. 1A and 1B). Morphologic images showing that amphiphilicity of an exemplary diblock PEG-PLA copolymer controls PNC morphology were obtained by transmission electron microscopy (TEM) with uranyl acetate staining (not shown). Spheroid particles resulted from a 63% PLA copolymer of mPEG (5K) and PLA (8.5K). Spheroid particles resulted from a 78.5% PLA copolymer of mPEG (5K) and PLA (18K). A mixed spherical/filamentous particle population was obtained with a 81% PLA copolymer of mPEG (5K) and PLA (21K). Filamentous particles were obtained with a 84% PLA copolymer of mPEG (5K) and PLA (27K). Filamentous particles were obtained with a 93% PLA copolymer of mPEG (5K) and PLA (64K). A transition from spherical (60-79 wt % of the hydrophobic polymer block, e.g., PLA) to mixed populations (80-81% PLA) to filamentous structures (>81-95% PLA) was seen with increasing PLA content measured by weight percentage of the total amphiphilic diblock copolymer. These photomicrographs were published as FIG. 2 in Simone et al 2007, cited above.

Final PNC concentration in the nano-scale fraction of the particles was determined by quantitative analysis of PEG or lactic acid content. For the 100% PLA PNC, polymer mass was determined solely by measuring lactic acid content. For the diblock copolymers, either assay could be used to measure total polymer mass in the PNC, due to the equimolar ratio of the PEG block to the PLA block. For example, using a PEG assay, the total mass of a diblock made with 5,000 Da PEG would be $$\text{Diblock } MW = \left\{ \frac{x(\text{g, } PEG)}{5000(\text{g/mol, } PEG)} \times [y(\text{g/mol, } PLA)] \right\} + [x(\text{g, } PEG)].$$

The inventors found that diblocks containing 60 to 100% PLA provided a significant yield (FIG. 1A) of nano-scale particles with mean diameters ranging from 200 to 600 nm (FIG. 1B). A peak in yield and in effective diameter was also seen at ~80-90% PLA.

PLA MW determined PNC geometry in the range of 63-93% PLA content. An increase in hydrophobic PLA fraction above 80% resulted in an abrupt shift from spherical geometry to filamentous structures, evident from fluorescence microscopy (FIG. 1B, inset) and TEM (figure not shown). The asymmetric morphology of PNC formed at >80% PLA complicates simple interpretation of DLS measurements (FIG. 1B) since the usual Stokes-Einstein equation assumes a spherical hydrodynamic radius. Therefore, size of filamentous PNC was estimated by microscopy. Fluorescence microscopy revealed that PNC with filamentous morphology are flexible in solution, similar to other PEG-diblock based filamentous micelles (Dalhaimer et al 2003, cited above; Dalhaimer, P. et al, *Journal of Polymer Science Part B-Polymer Physics* 2004, 42, (1), 168-176); and TEM of dried PNC shows the assemblies are not only filamentous, but also sufficiently robust to withstand drying.

EXAMPLE 10

PLA Content in PLA-PEG Co-Polymer Modulates PNC Loading and Activity of Loaded Enzymes In order to circulate in the bloodstream without mechanical retention in capillaries, spherical-PNC should be submicron in diameter. The homogenization in the double emulsion formulation produces PNC of desired size (200-500 nm), yet also reduces enzyme activity and decreases loading of the enzyme drug. The freeze-thaw cycle aids synthesis of enzyme-loaded PNC by both enhancing the amount of loaded enzyme and protecting it from inactivation (Dziubla et al 2005, cited above). Here the inventors tested how loading and resultant activity of the catalase depend on the content of hydrophobic PLA in the PLA-PEG copolymer.

The inventors monitored PNC loading, defined here as the percent of catalase added in the primary emulsion that is entrapped in the nano fraction of formulated particles, via radioisotope tracing of $^{125}$I-labeled catalase. The enzyme mass loaded in the microsphere population was excluded from this study, as this regime is not useful for the intended drug delivery application of this technology platform. Catalase loading showed a minor peak at 80% PLA and a major peak at 93% PLA. The lowest loading occurred at the extremes of 0 and 100% PLA, respectively.

Figures 2A, 2B, 2C:
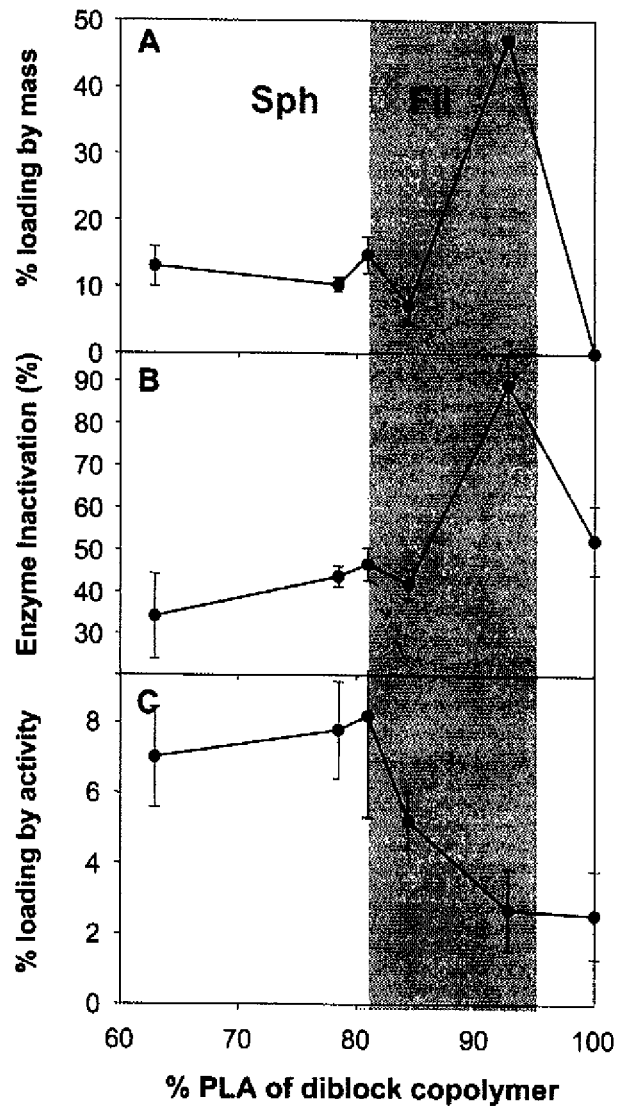
FIGS. 2A-2C show that amphiphilicity of exemplary diblock PEG-PLA copolymer controls PNC loading of an illustrative enzyme, i.e., catalase.
Figure 3A:
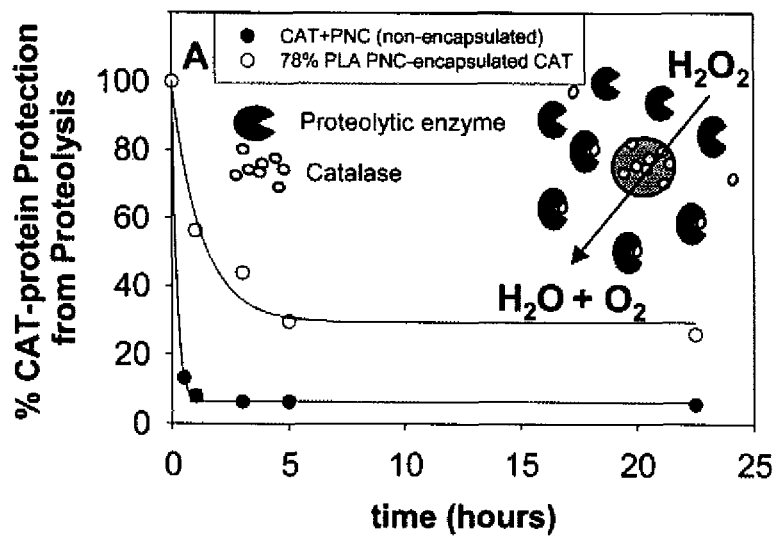
FIGS. 3A-3B are graphs showing that PNC protect catalase (CAT) from proteolytic degradation by pronase.

The highest catalase loading, 46.9%, was observed with 93% PLA (FIG. 3A). This result may represent both encapsulation and surface adsorption due to the enhanced hydrophobic nature of the dominant PLA block. Loading in the sub-60% PLA polymers was negligible (FIG. 3A), since PNC did not readily form in this range (FIG. 1A). When the PLA content was between 60-79% PLA, ≤500 nm spherical PNC were formed with an enzyme loading of 10%, similar to that reported in our previous study on loading catalase into PEG-PL(G)A PNC (Dziubla et al 2005, cited above). When the PLA content was increased over 81%, homogeneous filamentous PNC were formed (FIGS. 2A-2C) with an enzyme loading of 7.2% (for 84% PLA), a loading value similar to that of the spherical PNC.

Figure 3B:
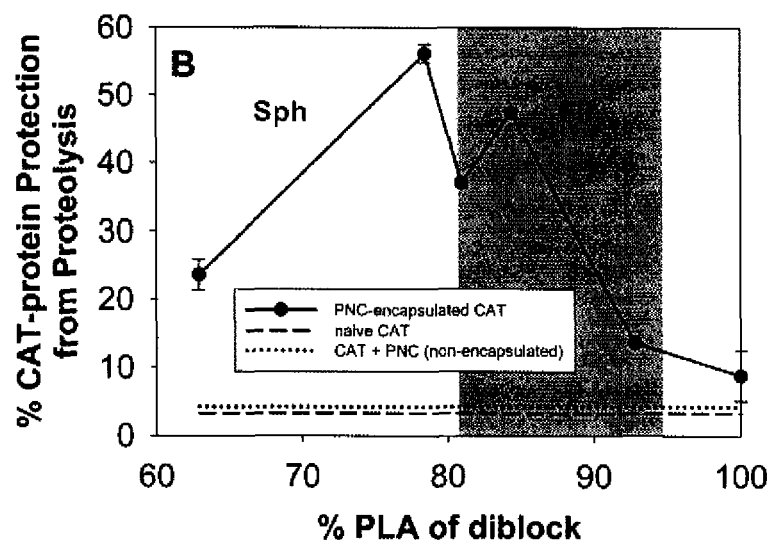
Figure 5:
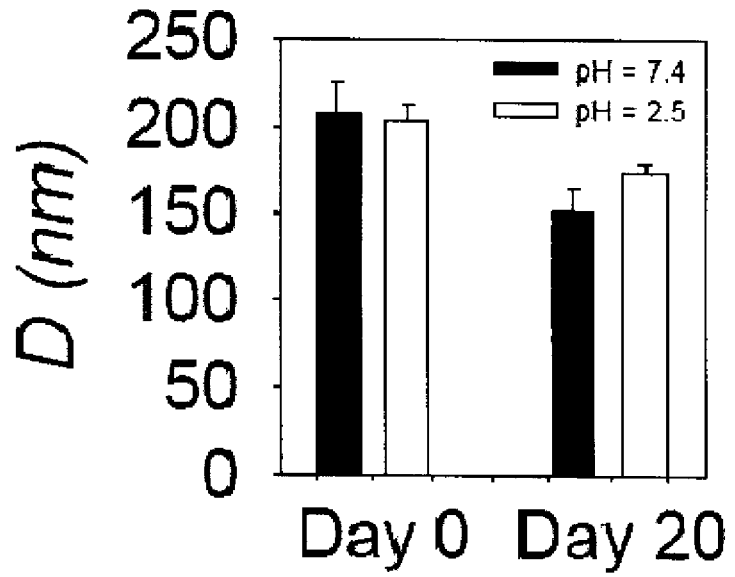
FIG. 5 is a bar graph showing effective diameters of degrading spherical ANC prepared by the methods disclosed herein exposed to two different pH conditions at Day 0 and Day 20. Initial and final sizes of degrading PNC are shown. There is very little change between initial and final time points, in terms of absolute diameter, even at very acidic pH.

Important for function, the level of enzyme inactivation during encapsulation also varied as a function of PLA content. Activity loss was the lowest (34.1±10.2% to 41.8±3.6%) between 63% and 84% PLA (FIG. 3B). Compositions with PLA MW from 20 to 50% PLA, where there was a negligible PNC yield, caused profound enzyme inactivation (up to or equal to 90.9±1.2% activity loss, data not shown), possibly due to the enhanced surfactant nature of the polymers that could affect the protein tertiary structure. Similarly, 89.1±6.8% inactivation was observed when the highly hydrophobic 93% PLA polymer was utilized.

Therefore, PLA MW in the diblock regulated catalase loading (FIG. 3A) and resultant activity of the loaded enzyme (FIG. 3B). In order to normalize activity per loading the inventors defined percent of loaded activity as:

$$\% \text{ Loading} = \left( \frac{\text{activity recovered in } PNC}{\text{added activity}} \right) \times (\% \text{ activity recovered})$$

where % activity recovered factors in activity lost in the homogenization/formulation process. To the best of our knowledge, this method of loaded-catalase quantification has not been reported before, and it provides a more therapeutically relevant measure of enzyme loading, compared to protein mass loaded. The analysis shows that the percent of loaded activity was relatively high (approximately 5.2±0.8-8.2±2.9%) in the optimal range of 63-84% PLA polymers (FIG. 3C).

EXAMPLE 11

Protection of Loaded Enzyme Against External Proteolysis

In the next series of experiments the inventors tested whether PLA content controlled the extent of protection of PNC-catalase against external proteolysis. First, the inventors determined the kinetics of proteolytic inactivation of catalase loaded into 78% PLA PNC (FIG. 4A). Free catalase was completely inactivated after incubation for one hour with the wide-spectrum protease, pronase, and thus this time is sufficient to test protection of PNC-encapsulated catalase against proteolysis. In this assay, formulations with a low PLA fraction (<60%) provided no measurable protection of catalase (not shown), presumably due to a lack of PNC formation (see FIG. 1A). The marginal protection observed at 100% PLA PNC is indicative of primarily surface adsorbed catalase, with no appreciable encapsulation to provide a physical barrier between catalase and a protease. This observation agrees with the proposed mechanism of encapsulation outlined above that requires a well defined amphiphile, which 100% PLA is not.

Loading of catalase into PNC produced with 63 to 84% PLA copolymer afforded significant protection against proteolysis (FIG. 4B). Loading catalase into PNC produced with 93% PLA copolymer provided little protection (13.6±0.3%), consistent with the hypothesis that the major fraction of the enzyme is surface-adsorbed in this rather hydrophobic filamentous PNC species. However, loading of catalase into either spherical or filamentous PNC, formed at 78% and 84% PLA, respectively, correspondingly provided 56.2±1.4% and 47.5±0.7% protection against proteolysis. Adding unloaded PNC to free catalase provided no protection against proteolysis (FIG. 4B, dashed lines), indicating that catalase adsorption on the PNC surface does not provide a secondary protective effect.

EXAMPLE 12

PLA Content, pH of the Medium and PNC Geometry Modulate PNC Degradation

To characterize copolymer PLA content control of PNC stability at physiologically relevant pH levels, degradation studies were performed at pH 7.4, 5.0, and 2.5, corresponding to normal blood plasma, lysosomal and stomach pH, respectively. DLS analysis of spherical PNC stability revealed a detectable decrease in the scattering intensity that can be directly correlated with the number of PNC in solution (FIG. 4A). There was only a marginal change in diameter of these spherical PNC over time, regardless of pH (FIG. 4B). This result likely reflects pH-modulated PNC degradation via bulk erosion rather than surface erosion. Thus, PNC with lower PLA MW (~80% PLA) decreased in number more rapidly with decreasing pH; the number of 80% PLA PNC dropped by ~35% at neutral pH, while at pH 2.5, the number of PNC decreased ~45% with a faster initial drop within the first week. Degradation at pH 5.0 was not significantly different than that at neutral pH (data not shown).

DLS analysis of filamentous PNC is complicated by their geometry and dynamic conformations in solutions. Thus, the effective size of filamentous PNC represents a complex function of their length, flexibility and coiling. Nevertheless, DLS measurements showed little change in either effective size or concentration of filamentous PNC formed at high PLA content (87% PLA) when incubated at neutral pH over a month (FIG. 4C,4D, black circles). Importantly, electron microscopy confirmed this result (not shown). In contrast, DLS analysis revealed a notable decrease in effective size of filamentous PNC at acidic pH, which correlated with an increase in the scattering intensity. This increased scattering implies an increased concentration of particulate matter, likely reflecting fragmentation of filamentous PNC (FIG. 4C,4D, white circles). Again, this DLS result has been confirmed by electron microscopy that showed a gradual fractionation of filamentous PNC into shorter and eventually spherical structures. This degradation phenomenon was typical of multiple formulations of filamentous PNC with even higher PLA content. Photomicrographs showing degradation of high MW (93% PLA) filamentous PNC over 21 days at two pH conditions were also obtained by the inventors (not shown). Such photomicrographs show condition of the PNC on Day 0 at pH 2.5 and 7.4; condition of the PNC on Day 7 at pH 2.5 and 7.4; condition of the PNC on Day 14 at pH 2.5 and 7.4; and condition of the PNC on Day 21 at pH 2.5 and 7.4, respectively. Higher MW (93% PLA) filamentous PNC show slightly higher resistance to degradation than lower MW filamentous PNC at low pH, as demonstrated through slower transition to vesicles over time. Overall, trends are similar to lower MW filamentous PNC with no change at neutral pH and a transition to shorter filaments and vesicles at acidic pH.

Thus, the inventors found that control of a diblock copolymer's amphiphilicity, through tuning of the ratio of hydrophobic to hydrophilic domains, led to morphology control in an alternative, modified emulsion formulation. Specifically, either spherical or filamentous polymer nanocarriers, PNC or f-PNC, respectively, were formed with what are believed to be interior aqueous domains, unique to this formulation. Within these domains, the hydrophilic and highly potent, yet labile 250 kDa antioxidant enzyme, catalase was not only encapsulated, but resistant to external proteolytic degradation upon PNC or f-PNC loading. It should be noted that this class of carrier is not designed for traditional "drug release", but rather serves as a protective cage wherein the enzyme substrate, $H_2O_2$, is readily diffusible through the polymer shell. These carriers were made from degradable poly(ether-b-ester) polymers, namely poly(ethylene glycol-b-lactic acid), or PEG-PLA.

EXAMPLE 13

Loading PEG-Catalase into Filamentous and Spherical Polymer Nanocarriers

These experiments were designed to test whether catalase replacement by PEG-catalase enhances the encapsulation efficiency and minimizes the surface accessible enzyme fraction in PEG-PLA PNC, and to examine PEG-catalase loading into morphologically different PNC, filamentous or spherical. This experiments characterized PNC/PEG-catalase drug delivery systems in terms of protein loading, morphology, activity and susceptibility of loaded enzyme to protease degradation, and circulation in vivo in a mouse model. The inventors considered that PEG-catalase may preferentially partition into PEG cores of the initial emulsion stabilized by the negative temperature transition from the first to the second emulsion of the nanocarrier forming process. This is an important advantage over the current double emulsion approach in which catalase encapsulation into PNC is associated with surface deposition of a significant fraction of the enzyme that is not protected from proteases.

In these experiments, methoxy-PEG (mPEG) MW 5,000 was purchased from Polysciences (Warrington, Pa.). Catalase from bovine liver and horseradish peroxidase were purchased from Calbiochem (EMD Biosciences, San Diego, Calif.). Uranyl acetate was acquired from Electron Microscopy Sciences (Fort Washington, Pa.).

The above described freeze-thaw modified double emulsion technique was utilized to encapsulate either the catalytically active enzyme catalase (MW ~250 kDa) or PEG-catalase in PEG-PLA polymer nanocarriers (PNC). Spectrophotometer measurement of substrate depletion was utilized to monitor enzyme activity. Isotope labeling of the enzyme was used in conjunction with activity measurements to determine PNC loading efficiency and PNC-enzyme resistance to proteases. This labeling also enabled blood clearance measurements of PNC-loaded and non-loaded enzymes in mice.

Synthesis of diblock copolymers was performed as follows: DL-lactide was precipitated twice into anhydrous diethyl ether, before mixing with mPEG in stoichiometric ratios to achieve desired molecular weights. Reactants were purged with dry nitrogen and sealed in a round bottom flask before heated to 140° C. while stirring for two hours to remove trace water from samples. The temperature was reduced to 130° C. and stannous octoate (1 wt %) was added to catalyze the ring opening polymerization (ROP) of lactide with mPEG serving as the initiator. The polymerization was allowed to continue for six hours. The diblock copolymer was then dissolved in DCM and twice precipitated in cold diethyl ether. Residual solvent was then removed by first drying via rotary evaporation (SafetyVap 205, Buchi, Switzerland), followed by lyophilization (VirTis BenchTop SLC, SP Industries, Gardiner, N.Y.).

Number average molecular weights ($\overline{M_n}$) of bulk copolymers were determined using proton nuclear magnetic resonance ($^1$H-NMR). The weight average molecular weights ($\overline{M_w}$) and polydispersity indices (PDI) were also determined by gel permeation chromatography (HPLC-GPC), with a Binary HPLC pump (1525, Waters, Milford, Mass.), a Refractive Index Detector (2414, Waters) and three serial 7.8×300 mm Styragel columns (Waters) using tetrahydrofuran (THE) as the mobile phase. Chromatograms were analyzed using Breeze version 3.3 software with polystyrene standards used for calibration.

The diffusivity of $H_2O_2$ through PEG-PLA was determined with a two diffusion chamber apparatus, as described before (Belland and Peppas 1996 *Biomater.*, 17:1203-18). Briefly, for each experiment, a new thin polymer film was cast and the thickness measured, before placement between two chambers, the donor containing the substrate, 5 mM $H_2O_2$ in pH 7.4 50 mM phosphate buffered saline (PBS), and the receptor containing simply 50 mM PBS. The two-cell apparatus was maintained at physiologic temperature. The concentration of $H_2O_2$ in the receptor compartment was determined as a function of time by measuring UV absorbance at 242 nm (Cary 50 UV-Vis, Varian, Palo Alto, Calif.).

Nanoparticles were prepared substantially as described above. The freeze-thaw double emulsion solvent evaporation technique involved dissolving mPEG-PLA diblock copolymer in DCM at 25 mg/ml. A 1 mg/ml catalase, or PEG-catalase (PEG $\overline{M_n}$=5,000, ~40 PEG molecules per protein molecule according to supplier) solution and a PVA surfactant solution (2 wt %, 87-89% hydrolyzed, $\overline{M_w}$=13,000-23,000) in 20 mM PBS are prepared. The primary emulsion consists of the organic phase (1 ml polymer—DCM mixture) and the aqueous phase (100 µl catalase solution) homogenized at 15,000 rpm for 1 minute in a dry ice-acetone bath with a 7 mm—blade homogenizer (Kinemetica Polytron 3100 with a PDTA3007/2 generator, Brinkmann Instruments, Westbury, N.Y.). The primary emulsion is then added to 5 ml of the PVA surfactant solution and homogenized at 15,000 rpm for 1 minute. The resultant mixture is added to 10 ml of PVA solution and stirred overnight to allow removal of the residual solvent. The microparticle fraction is removed by a primary centrifugation at 1,000 g for 10 minutes. The nanoparticle fraction is collected by subsequent centrifugation at 20,000 g for 30 minutes. The supernatant is then removed and the PNC pellet is re-suspended in PBS and purified again by further centrifugation.

Protein (enzyme) loading was determined via radioisotope labeling and enzymatic activity. Loading via radiolabeling was determined as described before, by formulating PNC with $^{125}$I-labeled catalase (Dziubla 2005, cited above) or PEG-cat. Catalase or PEG-cat was radiolabeled with Na$^{125}$I (Perkin Elmer, Boston, Mass.) via the Iodogen method (Pierce Biotech., Rockford, Ill.). Unbound $^{125}$I was removed from the enzyme using Biospin 6 columns in accordance with the manufacturer's instructions (Bio-Rad labs, Hercules, Calif.). Total solution $^{125}$I-catalase content was measured before centrifugation, and then radioactivity of the $^{125}$I-catalase/PNC-composed pellet after centrifugation was measured. A Wizard 1470 gamma counter (Wallac, Oy, Turku, Finland) was used for radiotracing.

To determine loading via enzymatic activity, a catalase activity assay (Shuvaev 2004 cited above; Beers and Sizer 1952 *J. Biol. Chem.*, 195(1):133-140) was used, both for the total sample before and after centrifugation. Briefly, 990 µl of 5 mM $H_2O_2$ in PBS and 10 µl of enzyme-loaded PNC was added to a quartz cuvette. The kinetics of $H_2O_2$ degradation was then measured with a spectrophotometer at 242 nm (absorbance at this wavelength corresponds to the $H_2O_2$ concentration and thus catalase activity, U/mg=23.0($\Delta A_{242}$/min)/mg of catalase).

Catalase protection against proteolysis was tested as described previously (Dziubla 2005, cited above). Briefly, PNC preps loaded with $^{125}$I-catalase were incubated with a 0.2 wt % pronase solution at 37° C. in a shaker bath set at 60 rpm for 1 hour. Samples were removed and centrifuged at 16,000 g for 20 minutes. Supernatant containing degraded protein and pellet containing intact protein encapsulated within PNC were collected and counted. This measure correlates linearly with preservation of enzymatic activity (Dziubla 2005, cited above; Dziubla et al, 2008 *Biomater.* 29(2): 215-27).

PNC size determination was made via dynamic light scattering (DLS, 90Plus Particle Sizer, Brookhaven Instruments, Holtsville, N.Y.) as described previously (Dziubla 2005, cited above; Simone 2007, cited above).

PNC concentration/yield was determined by a colorimetric assay based on the detection of lactic acid monomer (Barker and Summerson 1941 *J. Biol. Chem.*, 138:535-554). PEG-PLA samples were hydrolyzed to their monomer state with 5 M NaOH at 80° C. overnight and neutralized with 5 M HCl. One ml of 20 wt % $CuSO_4$ was added to a 1 ml aliquot of the hydrolyzed sample, alongside standards of known concentrations of lactic acid to construct a calibration curve. Samples were diluted to 10 ml, before addition of 1 g of dry $Ca(OH)_2$. After incubation at room temperature for 30 minutes, samples were centrifuged at 1000 g for 5 min and 1 ml aliquots of the supernatant were taken. 50 µl of 4 wt % $CuSO_4$ and 6 ml of sulfuric acid were sequentially added before incubation at 100° C. for 5 minutes. Samples were subsequently cooled to room temperature and 100 µl of p-hydroxydiphenyl in 0.5 wt % NaOH was added before a 30 minute incubation at 30° C. Next, the samples were heated to 100° C. for 90 seconds to dissolve excess hydroxydiphenyl. Once the samples cooled to 25° C., the lactic acid concentration was determined with a spectrophotometer at 560 nm.

PNC morphology was characterized by fluorescence microscopy, transmission electron microscopy (TEM), and scanning electron microscopy (SEM). For fluorescence microscopy, aliquots of PNC were stained with the lipophilic carbocyanine dye, PKH26, via established methods (Simone 2007, cited above; Dalheimer et al, 2003 *Macromol.*, 36(18): 6873-6877) and then imaged with a Nikon fluorescence microscope equipped with a 60× oil immersion objective. For TEM, samples were prepared as previously described above. Briefly, samples were immobilized on TEM mesh grids (Formvar Film 200 Mesh, Electron Microscopy Sciences, Hatfield, Pa.) and stained with filtered (0.1 µm filter) 2 wt % uranyl acetate. Grids were imaged on a TEM (JEOL JEM-100CX, West Chester, Pa.). For SEM sample preparation, PNC aliquots were lyophilized overnight and spread on a sample plate. Samples were sputter coated with platinum and imaged on a field-emission gun (FEG) environmental scanning electron microscope (ESEM, model XL30)

In vivo circulation and biodistribution studies were performed by loading PNC with $^{125}$I-catalase or $^{125}$I-PEG-catalase and i.v. injecting (tail vein, 50 mg polymer/kg bodyweight) into C57/BL6 mice following an IACUC approved protocol that adhered to the "Principles of Laboratory Animal Care" (NIH publication #85-23, revised in 1985). Non-PNC-encapsulated $^{125}$I-catalase and $^{125}$I-PEG-cat were also injected. Blood was drawn in 100 µl aliquots at specified increments from one minute to three hours by retro-orbital bleeding. At the end of the experiment, mice were sacrificed and harvested organs were washed, weighed and radioactivity measured. Five mice per experimental group were tested. Statistical significance was tested in all studies via a t test, where p values<0.05 were considered significant.

The results of these experiments were as follows: Non-loaded PEG-catalase exhibited longer circulation times than catalase, but was equally susceptible to proteolysis. Modulation of the ratio of relatively hydrophilic to hydrophobic domains in the diblock PEG-PLA copolymer provided either filamentous or spherical PNC loaded with PEG-catalase. For both PNC geometries, encapsulation and resistance to proteases of the resultant PNC-loaded enzyme were more effective for PEG-catalase than catalase. Isotope tracing showed similar blood levels of PNC-loaded and free PEG-catalase in mice.

By controlling reaction feed ratios, ring-opening polymerization (ROP) of lactide with a monomethoxy-capped mPEG initiator yielded mPEG-PLA with PLA block MW's of approximately 18,000 and 27,000 Da (see Table 2) as determined by $^{1}$H-NMR. The resultant wt % PLA, or "% PLA", defined as the ratio of PLA MW to the total diblock MW, is also shown in Table 2. The GPC-determined polydispersity indices of the polymers were both 1.5. MW of the PEG block was kept constant at 5,000 Da. Polymer MW schemes were selected from previous work to formulate either spherical or filamentous PNC loaded with active catalase, also outlined in Table 2. Definitions of the symbols used in Table 2 are as defined above for those of Table 1. The PNC morphology that results from the indicated polymer compositions is also noted.

TABLE 2

Synthesized Polymer Characterization

| Target PLA $\overline{M_n}$ | PLA $\overline{M_n}^a$ | % PLA | PLA $\overline{M_w}^b$ | PLA $\overline{M_w}^a$ | PDI | PNC Morphology |
|---|---|---|---|---|---|---|
| 20000.0 | 17895.6 | 78.2 | 23236.7 | 36908.2 | 1.5 | Spherical |
| 30000.0 | 27091.3 | 84.4 | 21859.0 | 35792.4 | 1.5 | Filamentous |

$^a$indicates that the measurement was determined by $^1$H-NMR
$^b$indicates that the measurement was determined by GPC.

The formulation scheme for nanocarrier synthesis and protein encapsulation utilized throughout these studies, and how PEGylation of the cargo may influence this is summarized as follows: In theory, during this freeze-cycle, the primary emulsion, 90% organic phase/10% aqueous phase, consists of inverse micelles of the amphiphilic diblock PEG-PLA copolymer with a PEG-core containing the hydrophilic enzyme. Thus PEGylated proteins would preferentially distribute within these PEG cores, stabilized by the −80° C. cycle. Furthermore, it is known that negative temperature transitions favor the formation of PEG hydrates and thus PEGylated catalase loading should benefit from the phase alignment of this synthesis scheme. For the therapeutic effect without cargo release, the key parameter is that the enzyme substrate (H$_2$O$_2$) diffuses freely through the PNC matrix.

A critical parameter of this protective cage delivery system is the diffusivity of the encapsulated enzyme's substrate through the polymer meshwork. Diffusivity of substrate through polymer material is determined via a two chamber diffusion experiment. Flux is derived from the solution to Fick's first law of diffusion for planar geometry, summarized in the following equation:

$$\ln\left(1 - \frac{2C_r}{C_d}\right) = -\frac{2Ak}{Vl}Dt$$

where $C_d$ and $C_r$ are donor and cumulative receptor cell concentrations, A is cross sectional area of the film at the port between the two cells, k is the partition coefficient, V is the receptor cell volume, l is the film thickness, D is the permeability coefficient, and t is time. The diffusivity, or permeability coefficient, D, is the slope of the flux curve of FIG. 6. While the absolute values of each data point fluctuate from each independent experiment, the important parameter, the slope of the corresponding trend line, D, is consistently on the same order of magnitude across all experiments. Measurement in this model showed that the normalized permeability coefficient of the catalase substrate, hydrogen peroxide, through the polymer material utilized for these formulations is on the order of $10^{-9}$ cm$^2$/sec.

Figure 7A:
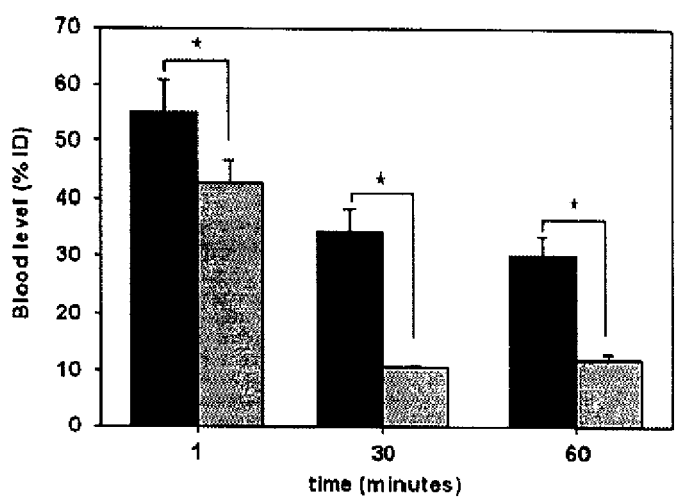
FIGS. 7A and 7B show the circulation and proteolytic resistance of PEG-catalase and unmodified catalase.
Figure 7B:
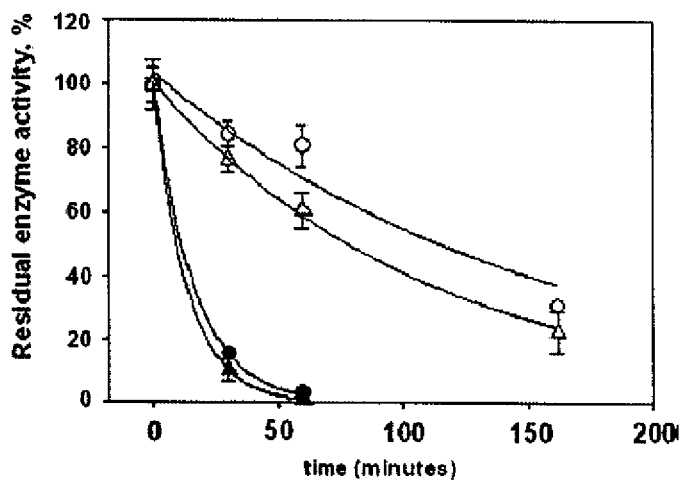

PEG-catalase circulates in vivo longer than catalase, but both PEG-catalase and catalase are susceptible to proteolysis. In the first series of experiments free PEG-catalase was compared with naive catalase without loading into PNC. Tracing of $^{125}$I-iodine labeled enzyme showed that PEG-catalase remains in the bloodstream at significantly higher levels than naïve catalase after intravenous injection in mice (P<0.02 at 1 minute post injection and P<0.001 thereafter, FIG. 7A). However, in vitro analysis showed that both free (non-loaded) PEG-catalase and catalase are rapidly degraded in proteolytic environments (FIG. 7B). Thus, one hour incubation with 0.2 wt % pronase caused 99.0±0.8% and 97.3±0.6% loss of activity of PEG-catalase and catalase, respectively. The rate of inactivation was similarly high for both enzymes at this protease concentration, which was typically used for testing the protective effect of PNC. Further, when the protease concentrations were reduced by an order of magnitude, inactivation was still rapid with a 69.5±1.5% (catalase) and 77.8±6.6% (PEG-catalase) loss of activity within three hours.

Figure 8A:
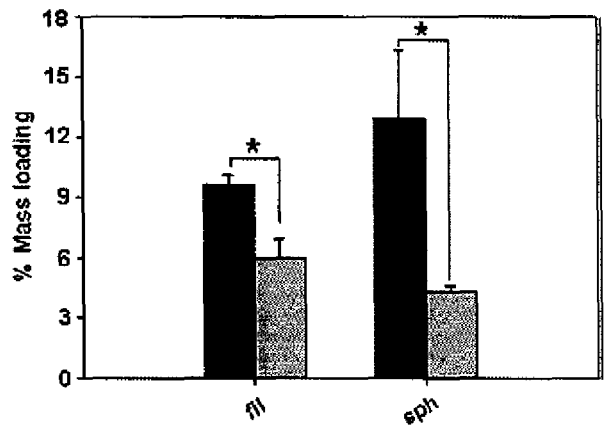
FIGS. 8A-8C show enzyme mass and activity loading.

PEG-catalase enhances PNC loading in a freeze-thaw modified formulation. Loading of $^{125}$I-labeled catalase or PEG-catalase into the nano-scale (<500 nm diameter) fraction of formulated PNC particles utilizing the methodology was monitored and analyses described above. FIG. 8A shows that the percent of loading by enzyme mass (defined as the percent of catalase added in the primary emulsion that is entrapped within PNC, or loading efficiency) was significantly enhanced for PEG-catalase vs catalase in both spherical (P<0.02) and filamentous PNC (P<0.001), by 200 and 100%, respectively.

Figure 8B:
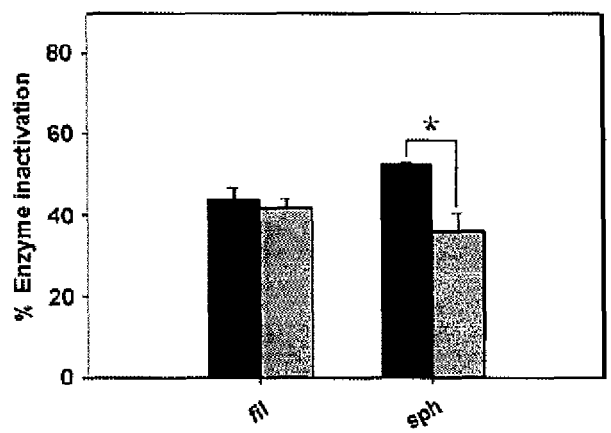

Retention of enzymatic activity through particle formulation was similar for the PNC encapsulated protein, regardless of PEGylation. There appeared to be little impact of the PEG modification of catalase. Catalase exhibited an activity of 23.3±2.8 kU/mg of protein while PEG-catalase demonstrated 21.5±1.1 kU/mg of protein. The degree of apparent enzyme inactivation during the encapsulation within filamentous PNC was similar for catalase and PEG-catalase. Inactivation was slightly higher for PEG-catalase relative to catalase loaded into spherical PNC (FIG. 8B). Redistribution of the PEG-catalase cargo from the PNC surface into the polymer matrix/PNC interior may augment diffusional limitations of substrate conversion, thereby overestimating PEG-catalase inactivation, as discussed below.

Figure 8C:
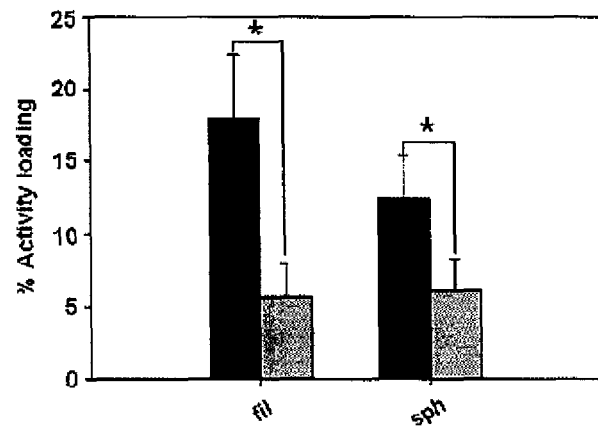

In order to normalize activity per loading percent of loaded activity was defined as:

$$\% \text{ Loading} = \left(\frac{\text{activity recovered in } PNC}{\text{total activity, post formulation}}\right) \times (\% \text{ apparent catalase inactivation})$$

where % apparent catalase inactivation factors in activity lost during the formulation process. This method of loaded-catalase quantification provides an ultimate measure of enzyme loading, i.e. total enzymatic activity associated with the PNC, taking into account formulation-induced inactivation. Thus, for both spherical and filamentous PNC, activity loading of PEG-catalase was significantly higher than that of naïve catalase (P<0.03, FIG. 8C).

Figure 9A:
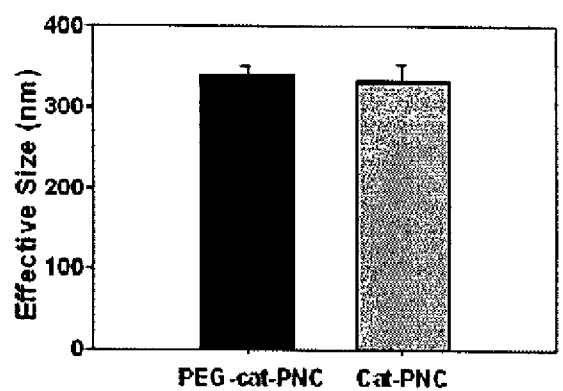
FIGS. 9A and 9B are bar graphs showing morphology of PNC with different enzyme cargoes.

Loading of PEG-catalase does not alter PNC morphology. As discussed above, PEGylated diblock copolymer amphiphilicity (and thus the ratio of PEG to PLA) has a profound effect on PNC morphology. Nevertheless, dynamic light scattering (DLS, FIG. 9A) and scanning electron microscopy (SEM, not shown) revealed no marked impact of PEG-enzyme on the size of spherical particles: i.e., the mean diameter of PNC loaded with PEG-catalase or catalase was ~350 nm. Similarly, transmission electron microscopy (TEM) and fluorescence microscopy revealed virtually identical morphologies for filamentous PNC loaded with either PEG-catalase or catalase (not shown). Cross sectional diameters varied between 60 and 70 nm for filamentous carriers with either cargo.

Final PNC concentration in the nano-scale fraction of the particles was determined by quantitative analysis of lactic acid content after complete hydrolysis of the PLA-PEG polyester carriers. Absolute mass yield was calculated based on the fact that PEG and PLA exist in equimolar amounts in the polymer backbone:

$$\text{Diblock polymer mass yield} = \left\{\frac{x(\text{g}, PLA)}{MW_{PLA}(\text{g/mol}, PLA)} \times [MW_{PEG}(\text{g/mol}, PEG)]\right\} + [x(\text{g}, PLA)]$$

Figure 9B:
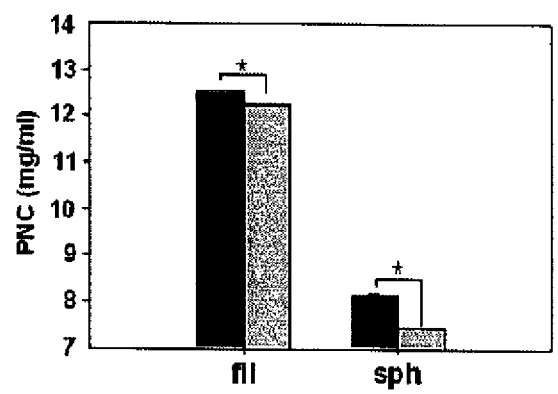

According to this analysis, there was a small, yet significant (P<0.001) increase in mass yield of PNC loaded with PEG-catalase compared to catalase for both filamentous and spherical carriers (FIG. 9B). Similar to the preceding examples, the ultimate yield of filamentous carriers was higher than that of spherical PNC.

Figure 10A:
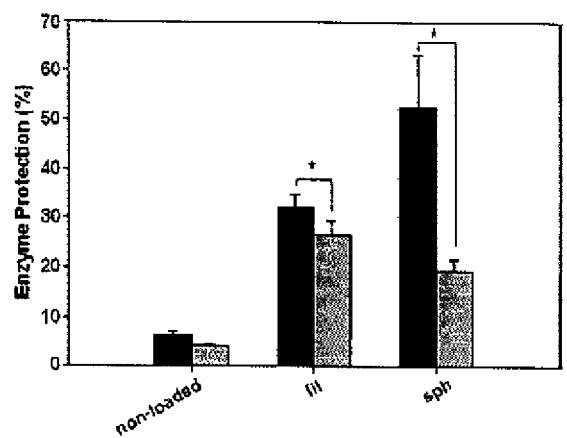
FIGS. 10A and 10B are bar graphs showing protective effect of PNC against external proteases and pharmacokinetics in mice.

PEG-catalase loaded in PNC was more resistant to proteases than catalase loaded in PNC, as shown in an in vitro test of protease inactivation used to compare the kinetics of proteolytic inactivation of PEG-catalase and catalase when loaded in PNC (FIG. 10A). Protection was determined after a one hour incubation of the PNC in a protease solution, as this time interval was previously determined to be adequate to distinguish PNC-encapsulated enzyme protection from that of non-encapsulated enzymes. PNC-loaded PEG-catalase demonstrated markedly higher resistance to proteolysis than PNC-loaded catalase. This effect was most pronounced with spherical PNC, providing more than a two-fold higher protection of PEG-catalase relative to catalase (P<0.005). Filamentous PNC also provided a significantly higher protection of PEG-catalase compared to catalase (P<0.01).

Figure 10B:
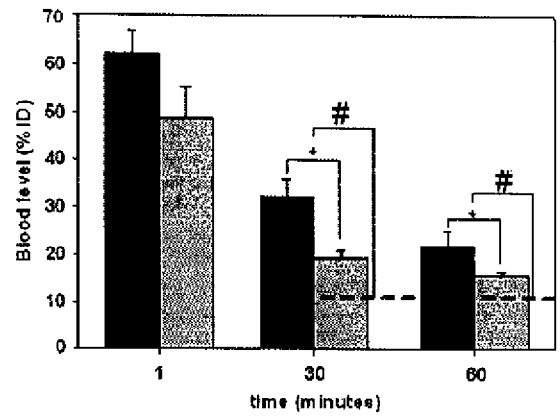

PEG-catalase-PNC and catalase-PNC circulate in mice. To test the potential utility of these formulations for intravascular drug delivery, $^{125}$I-labeled catalase or PEG-catalase loaded within PNC were injected intravenously in mice (FIG. 10B). Both formulations demonstrated significantly elevated levels in the blood relative to free catalase within the first hour post injection (P<0.001). Therefore, the circulation time of PNC loaded with either enzyme demonstrate a significant improvement relative to naive catalase that is not loaded within PNC (FIG. 10B, dashed line).

The hypothesis that PEG-catalase loads more efficiently than catalase into PEG-PLA PNC when such a formulation is used was tested here. The PNC preparations of different morphologies loaded at a far higher efficiency when PEG-catalase was utilized. The same trends in both loading and protection were also observed with PNC formulated from several other different molecular weight PEG-PLA copolymers that were tested (data not shown).

The relatively mild chemical modification of enzymes appears to be a solution to enhancing loading of potent biotherapeutics such as catalase into PNC, particularly if production of this delivery system were to reach an industrial scale. PEGylation of catalase is thought to occur primarily via lysine residues, with approximately 40 molecules of PEG per molecule of enzyme (as stated by the supplier, Sigma) in the preparations used in this study. At this extent of modification, PEGylation has minimal impact on specific activity of catalase, wherein both unmodified and PEGylated catalase exhibited specific activities on the order of 20 kU/mg protein. Protocols for such chemical modifications of enzymes have long been documented in the literature (Abuchowski et al, 1977 *J. Biol. Chem.* 252:3582-86; Pyatak et al, 1980 *Res. Commun. Chem. Pathol. Pharmacal.*, 29:113-27; Beckman et al, 1986 *J. Free Radic. Biol. Med.*, 2:359-65; Abuchowski et al, 1977 *J. Biol. Chem.* 252:3578-81) and many PEGylated enzymes, catalase included, are commercially available, thus suggesting that this would be a relatively simple modification to implement in an industrial setting.

These data show that use of PEG-catalase provides higher PNC loading and resistance to protease degradation than unmodified catalase. This trend was similar for both spherical and filamentous PNC, yet an interesting result of PNC morphology was noted. For instance, while inactivation of PEG-catalase loaded into filamentous PNC was minimal and indistinguishable from that of catalase, the gain in protease resistance was less impressive than in the case of spherical PNC. This outcome suggests that there exists a limit to filamentous PNC protection of its loaded protein, possibly due to the small (~60 nm diameter) cross section. This feature translates into a smaller protective barrier, or in other words, less polymer material between the encapsulated enzyme and any external proteases. Similarly, in the case of spherical PNC, the apparent inactivation of PEG-catalase from formulation was slightly higher than that of catalase. This apparent inactivation may be a reflection of an increase in the diffusion path length of the diffusing enzyme substrate $H_2O_2$ that results from deeper encapsulation of PEG-catalase within the PNC. For enzymes deeply embedded within the PNC, the polymer thickness that must be traversed in the sphere is approximately equal to R (the radius of the sphere). However, for the filamentous PNC, this value is equal to r (the radius of the filament cross section). From analysis of the DLS and electron microscopy data, R is approximately 150 nm while r is only 30 nm. This is exacerbated when one considers possible material limitations. For instance, polymer membrane diffusion studies suggest that there may be a minor diffusion limitation for $H_2O_2$ through the biomaterial matrix since the permeability coefficient through PEG-PLA is on the order of $10^{-9}$ cm$^2$/sec (FIG. 6), compared to $10^{-8}$ cm$^2$/sec (Seaver and Imlay 2001 *J. Bacterial.*, 183:7182-89) through a cell lipid bilayer. While this difference is small, if the utilization of PEG-catalase results in deeper embedment within the PNC, there is likely a modest increase in diffusion barrier, i.e. access of the substrate to the encapsulated enzyme. Given the rapid kinetics of catalase activity, even a minor diffusion barrier could result in some degree of apparent inactivation. Overall, this does not seem to be a major limiting factor and is consistent with the superior resistance of PEG-catalase to protease degradation when loaded within spherical PNC.

These results on prolonged circulation of PEG-catalase relative to catalase (FIG. 2A) are consistent with the literature reports that PEGylation of enzymes offers many solutions to the limitations of protein therapeutics, including prolongation of circulation, facilitation of intracellular delivery and protection against inactivation. However, these data show that PEG-catalase and catalase showed very similar susceptibilities to proteolysis, independent of protease concentration (FIG. 2B). Of note, PEGylation of fibrinogen did not prevent its proteolysis.

Spherical PNC in the sub-500 nm range are readily internalized when targeted to appropriate cell surface receptors and thus are plausible candidates for intracellular delivery. Furthermore, PNC of this size circulate well enough to target specific cell types when decorated with an affinity moiety, i.e. a peptide, antibody, antibody fragment, aptamer, etc. This is evident when one notes that these PNC, without any targeting ligands, circulate on the order of hours, while similar PNC decorated with targeting antibodies traffic to their specified destination within minutes of injection. Thus it would seem that the PEG-catalase-PNC, of approximately the same size as unmodified catalase-PNC, are prime candidates for systemic targeted therapeutics. Circulation studies show that there is a definite enhancement in circulation over non-loaded catalase when either PEG-catalase or catalase is encapsulated within PNC.

For nano filamentous carriers, there is tremendous drug loading capacity afforded by their long, micron scale length. Yet, the fact that they retain their nano status in terms of their cross sectional diameter, can result in very long circulating carriers with the potential for prolonged therapy (Geng et al, 2007 cited above). Furthermore, their high surface area to volume ratio indicates a high potential for surface decoration with targeting epitopes relative to the carrier mass and thus has tremendous potential for drug targeting.

This experiment demonstrates a new application for PEGylated enzymes, namely loading within polymer nanocarriers of unique filamentous and spherical morphologies. The goal of this study was to maximize encapsulation and minimize catalase surface absorption, and thus protease accessibility to the loaded enzyme, in PNC formulations. Enzymes modified with PEG succeed in this area, as well as in enhancing protein mass loading. Thus, a simple and well characterized modification results in a therapeutic enzyme-nanocarrier delivery system well suited for intravascular delivery.

EXAMPLE 14

Enzyme-Loaded Filaments with Tunable Features

These experiments demonstrate the development of enzyme-loaded filaments with tunable features including stiffness and length. The inventors tested whether PEG-PLA diblock copolymers of comparable composition to those that formulated f-PNC in previous studies, regardless of absolute MW, will still form filamentous carriers loaded with active catalase when the modified double emulsion formulation is utilized. The second experiment was performed to shown that modulation of the absolute polymer MW dictates mechanical properties of the carriers such as flexibility, or stiffness, as well as contour length. Filomicelles have some of these same dependencies on polymer molecular size (Dalheimer et al, 2003, cited above; Dalhaimer et al, 2004 *J. Polymer Sci. Part B*, 42(1):168-176), and thus it was plausible that such a phenomenon would translate over to f-PNC. This experiment shows for the first time development of a battery of different f-PNC with controllable physical features, all dependent on the polymer MW. Further, these carriers encapsulated an active, therapeutic enzyme, which was subsequently resistant to external protease degradation.

The physical properties of active enzyme-loaded filamentous PNC are controlled by polymer MW. In particular, stiffness, length, and cross sectional diameter can be finely tuned through alterations in the absolute polymer MW. Due to the unique thermal properties of the polymers utilized for carrier formation, the resultant f-PNC are quite flexible at physiologic temperatures. Furthermore, control of the polymer backbone structure enables protein-loadable filaments across a broad range of polymer MWs. This offers a new genre of non-spherical enzyme delivery devices, with applications both in targeting and sub-cellular addressing.

These experiments demonstrate the polymer MW control of two unique features of the particle formulation utilized. First, through maintenance of comparable ratios of hydrophobic to hydrophilic domains in the polymer, regardless of the absolute MW, enzyme-loaded filamentous PNC are possible. Second, the above-mentioned parameter of carrier stiffness is MW-tunable, i.e., increasing MW increases f-PNC flexibility in solution. Similarly, the contour lengths and cross sectional diameters of the f-PNC demonstrated polymer MW dependence, analogous to the MW-stiffness relationship. In addition to polymer MW reduction, sonication can also be utilized to reduce the length of these filamentous carriers (data not shown). Specifically, either spherical or filamentous polymer nanocarriers, PNC or f-PNC, respectively, were formed with what are believed to be interior aqueous domains, unique to this formulation. Within these domains, the hydrophilic and highly potent, yet labile 250 kDa antioxidant enzyme, catalase was not only encapsulated, but resistant to external proteolytic degradation upon PNC or f-PNC loading.

1,900 and 5,000 MW methoxy-PEG (mPEG) were obtained from Polysciences (Warrington, Pa.); 10,900 and 19,000 MW mPEG from Polymer Source (Dorval, Quebec, Canada), and catalase from bovine liver from Calbiochem (EMD Biosciences, San Diego, Calif.). Unless noted otherwise, all PBS solutions were 20 mM concentration.

Synthesis of diblock copolymers was performed as described above. Briefly, DL-lactide was precipitated twice into anhydrous diethyl ether, before mixing with different MW mPEG in stoichiometric ratios to achieve desired molecular weights. Reactants were purged with dry nitrogen and sealed in a round bottom flask before heated to 140° C. while stirring for two hours to remove trace water from samples. The temperature was reduced to 130° C. and stannous octoate (1 wt %) was added to catalyze the ring opening polymerization (ROP) of lactide with mPEG serving as the initiator. The polymerization was allowed to continue for six hours. The diblock copolymer was then dissolved in DCM and twice precipitated in cold diethyl ether. Residual solvent was then removed by first drying via rotary evaporation (Safety Vap 205, Buchi, Switzerland), followed by lyophilization (VirTis BenchTop SLC, SP Industries, Gardiner, N.Y.).

Number average molecular weights ($\overline{M_n}$) of bulk copolymers were determined using $^1$H-NMR. The weight average molecular weights ($\overline{M_w}$) and polydispersity indices (PDI) were also determined by gel permeation chromatography (HPLC-GPC), with a Binary HPLC pump (1525, Waters, Milford, Mass.), a Refractive Index Detector (2414, Waters) and three serial 7.8×300 mm Styragel columns (Waters) using tetrahydrofuran (THF) as the mobile phase. Chromatograms were analyzed using Breeze version 3.3 software with polystyrene standards used for calibration.

The glass transition ($T_g$) and melt temperature ($T_m$) thermal properties of the bulk polymer material were determined with a differential scanning calorimeter (DSC, DSC 2010, TA Instruments, New Castle, Del.). 10 mg polymer samples were crimped inside of standard non-hermetic aluminum pan/lid pairs (TA Instruments). Samples placed in the DSC were cooled to approximately −70° C. while under nitrogen. Subsequently, samples were heated to 120° C. at 20° C./min. The heat flow data was plotted against temperature. As the sample was heated from −70° C., after thermally stabilized (no endo/exothermic events, typically before the sample reached −60° C.) the $T_g$ was taken as the mid-point of the first endotherm, while the $T_m$ was the minimum of the second endotherm.

Nanoparticle formation used the freeze-thaw double emulsion solvent evaporation technique as described above. The primary emulsion consists of the organic phase (1 ml of a 25 mg/ml polymer-DCM solution) and the aqueous phase (100 µl of a 1 mg/ml catalase-PBS solution) homogenized at 15,000 rpm for 1 minute in a dry ice-acetone bath with a 7 mm—blade homogenizer (Kinematica Polytron 3100 with a PDTA3007/2 generator, Brinkmann Instruments, Westbury, N.Y.). The primary emulsion is then added to 5 ml of a 2 wt % PVA surfactant solution (87-89% hydrolyzed, $\overline{M_w}$=13,000-23,000, in PBS) and homogenized at 15,000 rpm for 1 minute. The resultant mixture is added to 10 ml of PVA solution and stirred overnight to allow residual solvent evaporation. The microparticle fraction is removed by a primary centrifugation at 1,000 g for 10 minutes and the nanoparticle fraction is collected by subsequent centrifugation at 20,000 g for 30 minutes. The supernatant is then removed and the PNC pellet is re-suspended in PBS and purified again by further centrifugation.

Enzyme loading was determined via isotope tracing and enzymatic activity. Loading via radiolabeling was determined as described before, by formulating PNC with $^{125}$I-labeled catalase (Dziubla 2005, cited above). Catalase was radiolabeled with Na$^{125}$I (Perkin Elmer, Boston, Mass.) via the Iodogen method (Pierce Biotech., Rockford, Ill.). Unbound $^{125}$I was removed from the enzyme using Biospin 6 columns in accordance with the manufacturer's instructions (Bio-Rad labs, Hercules, Calif.). Total solution $^{125}$I-catalase content was measured before centrifugation, and then radioactivity of the $^{125}$I-catalase/PNC-composed pellet after centrifugation was measured with a Wizard 1470 gamma counter (Wallac, Oy, Turku, Finland).

Enzymatic activity loading was determined via a catalase activity assay (Shuvaev 2004 cited above; Beers 1952 cited above) both for the total sample before and after centrifugation. The assay, based on substrate ($H_2O_2$) consumption, was performed by combining 990 µl of 5 mM $H_2O_2$ in PBS and 10 µl of enzyme-loaded PNC in a quartz cuvette. A spectrophotometer set to measure absorbance at 242 nm was used to determine the kinetics of $H_2O_2$ degradation (absorbance at this wavelength corresponds to the $H_2O_2$ concentration and thus catalase activity, U/mg=23.0($\Delta A_{242}$/min)/mg of catalase).

Catalase resistance to protease degradation was tested as described above. Briefly, PNC preps loaded with $^{125}$I-catalase were incubated with a 0.2 wt % pronase (a potent, non-specific protease) solution at 37° C. in a shaker bath set at 60 rpm for 1 hour. Samples were removed and centrifuged at 16,000 g for 20 minutes. Supernatant containing degraded protein and pellet containing intact protein encapsulated within PNC were collected and counted. This measure correlates linearly with preservation of enzymatic activity (Dziubla 2005, cited above; Dziubla 2008, cited above).

PNC morphology was characterized by fluorescence microscopy and transmission electron microscopy (TEM) techniques. For fluorescence microscopy, aliquots of PNC were stained with the lipophilic carbocyanine dye, PKH26, via methods described in examples above and in Dalheimer 2003 cited above). Images were taken in real time with an inverted epifluorescence microscope (TE2000-U Eclipse, Nikon Instruments, Inc., Melville, N.Y.) equipped with a 60× oil immersion objective, in conjunction with a UV lamp (Lambda DG-4, Sutter Instrument Co., Novato, Calif.) and a CCD camera (ORCA-ER C4742, Hamamatsu Corporation, Bridgewater, N.J.). For TEM, samples were prepared as described above. Briefly, samples were immobilized on TEM mesh grids (Formvar Film 200 Mesh, Electron Microscopy Sciences, Hatfield, Pa.). Staining was not necessary for visualization. Grids were imaged on a TEM (JEOL JEM-100CX, West Chester, Pa.).

PNC persistence and contour lengths were determined via established fluorescence techniques (Dalhaimer 2003 and 2004, both cited above) that utilized carriers stained with PKH26. Metamorph imaging software was used for time-lapse image acquisition. The corresponding stack files were exported in AVI format before analysis with ImageJ (NIH). Slides were treated with silicone (SigmaCote®, Sigma) to minimize non-specific immobilization of PNC on the glass. Thermal dependence microscopy studies were performed with a temperature stage (PDMI-2 Open Perfusion Micro-Incubator, Harvard Apparatus, Holliston, Mass.) and controller (TC-202A Temperature Controller, Harvard Apparatus). The stage contained 50 µl aliquots of PNC samples, pressed flat with a cover slip.

Effective length was determined via dynamic light scattering (DLS, 90Plus Particle Sizer, Brookhaven Instruments, Holtsville, N.Y.). Diffusion coefficients were determined from the light scattering intensity measurements of the DLS. These diffusion coefficients were used to calculate the effective length via the Stokes-Einstein equation, modified to approximate rod-like structures (Cai 2007, cited above; Li et al, 2004 *Phys. Rev. E. Stat. Nonlin. Soft Matter Phys.* 69 (6 Pt. 1), 061921).

A colorimetric PEG assay based on the PEG-Barium Iodide complex was utilized to determine PNC concentration as described in examples above. Two solutions were prepared: solution A, consisting of 2.4 g of Barium chloride, 8.0 ml of 6 M HCl and 32 ml of deionized (DI) water, and solution B, consisting of 800 mg of potassium iodide, 500 mg of iodine, and 40 ml of DI water. Aliquots of the PNC samples were added to a 96 well plate and diluted to a 170 µl it total volume with DI water. Subsequently, 40 µl of solution A and ⅕ diluted solution B were then added to each well. After a 10 minute incubation at 25° C., absorbance of the colored product was measured at 550 nm using a microplate reader (Model 2550-UV, Bio-Rad Labs, Hercules, Calif.) (Sims and Snape 1980, cited above). Standard solutions of PEG of known MW were used for calibration.

The results of these experiments were as follows. Ring-opening polymerization (ROP) of lactide with different MW monomethoxy-capped mPEG initiators (between 1,900 and 19,000 Da) yielded diblock mPEG-b-PLA polymers with total MW's ranging from approximately 12,000 to 89,000 Da (see Table 3) as determined by $^1$H-NMR. PLA MW was controlled via the stoichiometry of the reaction, i.e., control of the feed ratio of lactide and mPEG reagents determined the ultimate polymer block MW's. The resultant wt % PLA, or "% PLA", defined as the ratio of PLA MW to the total diblock MW, is also shown in Table 3. The target PLA fractions were determined based off of previous results that suggested these compositions might formulate filamentous PNC (f-PNC) loaded with active catalase as described in the preceding examples. The GPC-determined polydispersity indices of the polymers were between 1.5 and 1.7, typical of ROP products. Names of the individual polymers are also indicated in Table 3. Definitions of number average molecular weights, polydispersities, actual % PLA, or wt % PLA, are defined as in the prior examples. The corresponding MW methoxy end-capped mPEG utilized for each polymer is indicated in the first column. The nomenclature for each polymer is indicated in the last column.

TABLE 3

Synthesize Polymer Characterization

| PEG $M_n$ | Target PLA $M_n$ | PLA $M_n{}^a$ | % PLA | Total MW | PDI$^b$ | Name |
| --- | --- | --- | --- | --- | --- | --- |
| 1900.0 | 10000.0 | 10165.7 | 84.3 | 12065.7 | 1.7 | EL2-10 |
| 5000.0 | 30000.0 | 27091.3 | 84.4 | 32091.3 | 1.6 | EL5-27 |
| 10200.0 | 40000.0 | 40437.0 | 79.9 | 50637.0 | 1.6 | EL10-40 |
| 19000.0 | 70000.0 | 70095.3 | 78.7 | 89095.3 | 1.5 | EL19-70 |

$^a$determined by $^1$H-NMR
$^b$determined by GPC

Figure 11:
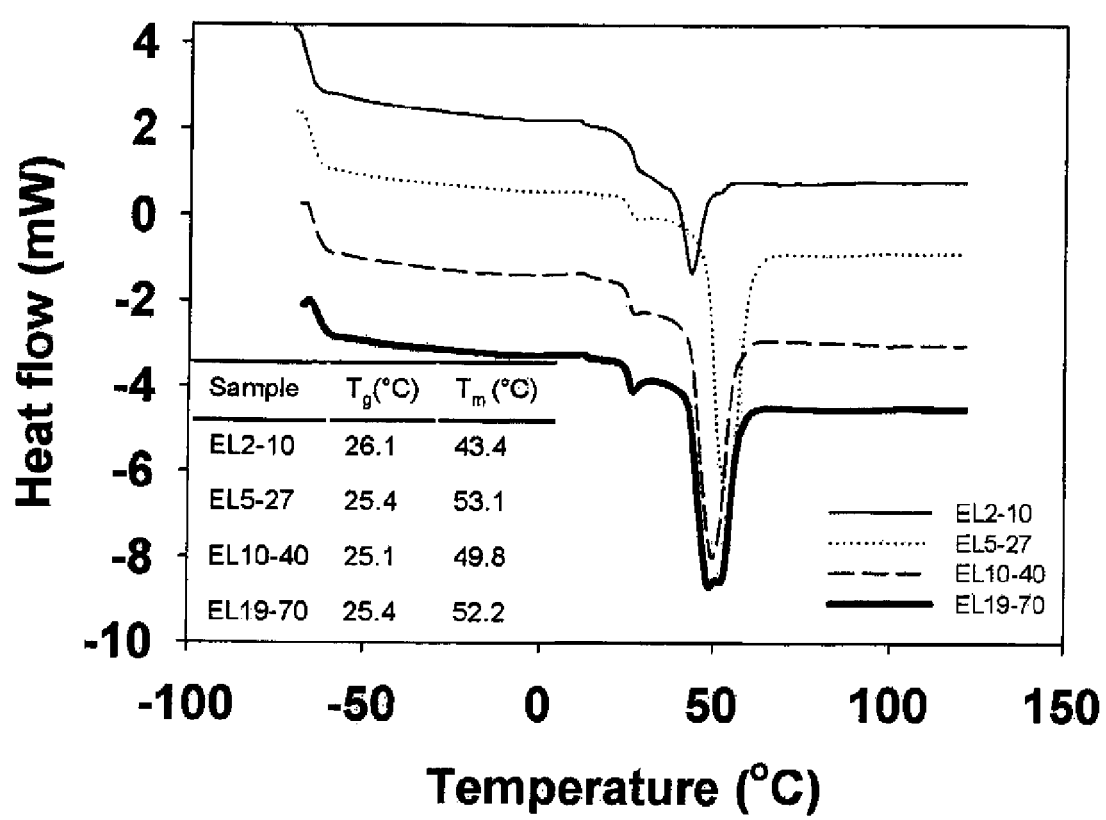
FIG. 11 is a graph showing DSC of PEG-PLA polymers of different MW polymers offset from one another for clarity. The inset table lists the glass transition temperature ($T_g$, from the first endotherm encountered upon sample heating) and melt temperature ($T_m$, from the second endotherm) of each polymer.

Thermal properties of the synthesized polymers were determined via differential scanning calorimetry (DSC, FIG. 11). As expected for these materials, only two thermal events were noted for each of the scanned polymers, namely the glass transition temperature ($T_g$) and the melt temperature ($T_m$). The first observed endotherm indicated that the $T_g$ was just above 25° C. for all of the tested polymers. The second endotherm indicated that the $T_m$ of the polymers ranged from 43° C. to 53° C. There did not appear to be any MW dependence of the thermal properties of these diblock copolymers.

Figure 12A:
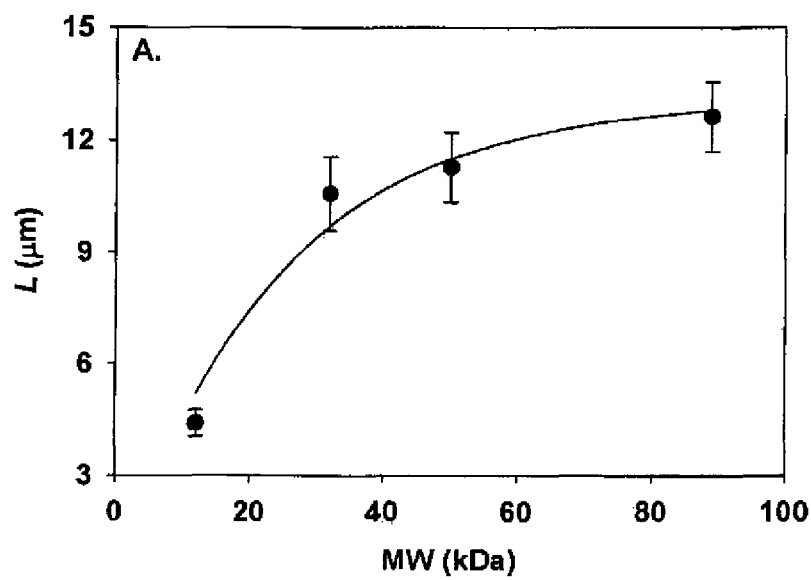
FIGS. 12A-12E are graphs showing that contour lengths of enzyme-loaded f-PNC are MW dependent.
Figure 12B:
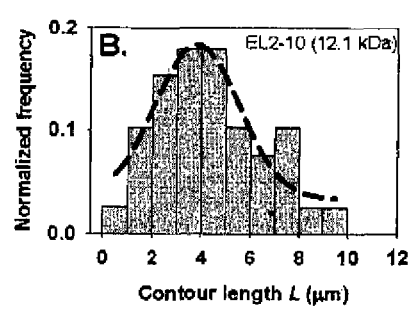
Figure 12C:
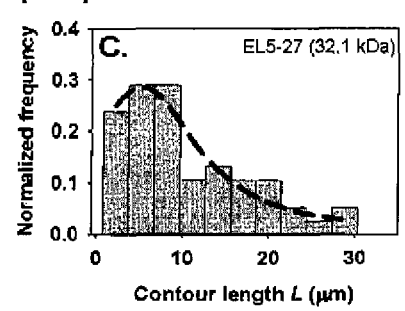
Figure 12D:
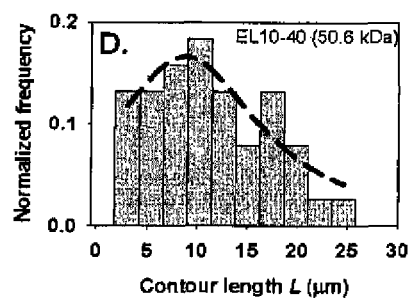
Figure 12E:
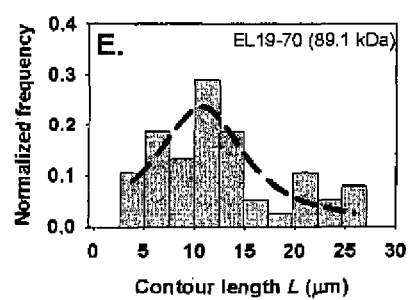

PEG-PLA diblocks of similar composition were found to form filamentous PNC, independent of absolute MW, yet the PNC contour and persistence lengths were MW and/or temperature dependent. The above described polymers were formulated into nanocarriers with a freeze-thaw modified double emulsion as described above and in Dziubla 2005 cited above. All four tested polymers indeed formed filamentous particles, as verified by fluorescence and electron microscopy (data not shown). While the general shape was similar, specific physical properties such as length and stiffness of the carriers differed dramatically. The contour length, L, of a nanofilament is defined here as the absolute length as traced along its backbone, FIG. 12A. Histograms of each different polymer sample show the distribution of L, FIG. 12B-12E. However, the trend is obvious when one looks at the average of each preparation, namely that there is a clear increase in contour length with increasing polymer MW, FIG. 12A. This effect appears to reach a plateau with increasing MW. The shortest L occurs with EL2-10 (12.1 kDa) at approximately 4.4±0.3 µm and is maximal at 12.6±0.9 µm for EL19-70 (89.1 kDa).

Figure 13:
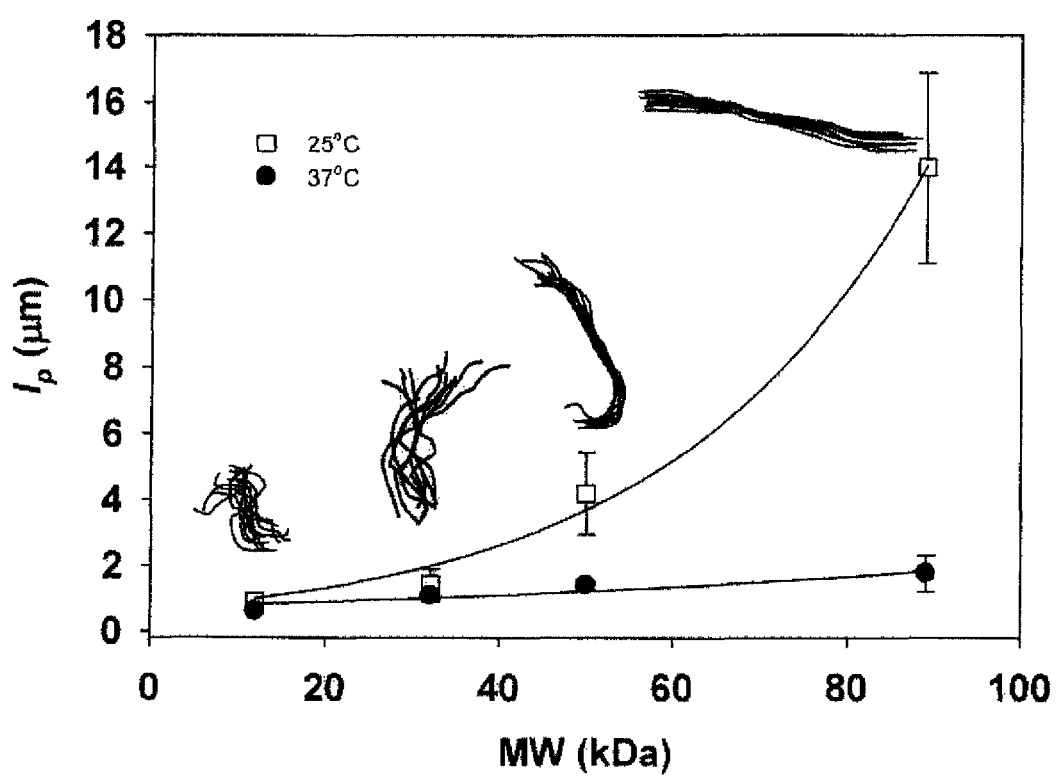
FIG. 13 is a graph showing that persistence lengths are MW and temperature dependent. Persistence lengths, $l_p$, are shown as a function of polymer MW. Results from two different temperatures are shown, one below (25° C., □) and one above (37° C., ●) the glass transition temperature of the polymer. Measurements were made from fluorescence time-lapse video analysis (not shown). Sample backbone traces of 10 consecutive frames, taken at 0.5 second intervals at 25° C., are overlaid and shown for each different MW f-PNC preparation.
Figure 14A:
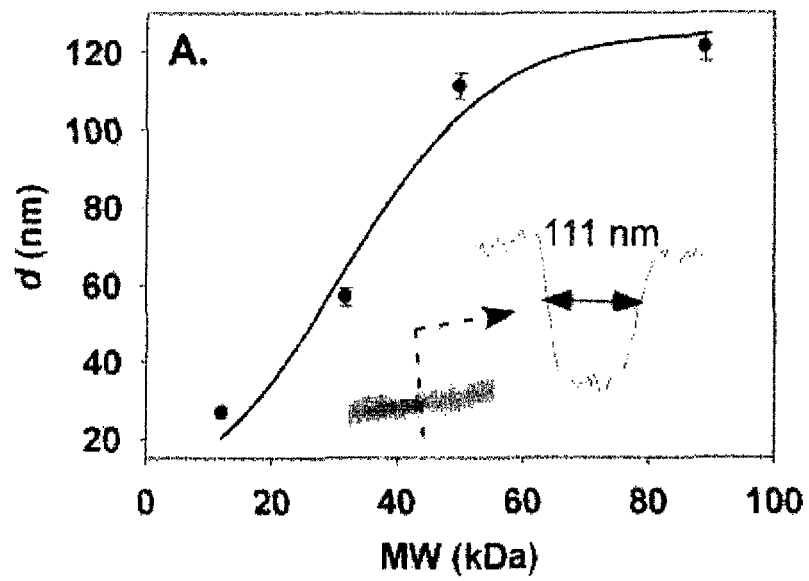
FIGS. 14A and B are graphs showing that cross sectional diameter and effective length are MW dependent.

Another important parameter when characterizing filaments is their stiffness, quantified by the persistence length, $l_p$, where a shorter $l_p$ correlates to a more flexible carrier while longer $l_p$ correlates to a stiffer carrier. $l_p$ is related to L and R, the end-to-end distance of a filament, by the following equation:

$$\langle R^2 \rangle = 2 l_p^2 \left[ \frac{L}{l_p} - 1 + \exp\left(-\frac{L}{l_p}\right) \right] \qquad \text{(i)}$$

where $l_p$ is divided by two due to the pseudo two dimensional confinement of the f-PNC sample between coverslips (Dalhaimer et al 2003 and 2004 both cited above; Wilhelm 1996 Phys. Rev. Lett 77(12):2581-2584; Grosberg et al, 1994 Stat. Phys. Macromol, AIP Press: New York). Measurements are made from time-lapse fluorescence microscopy images. In order to illustrate the degree of fluctuation in conformation of these carriers, ten superimposed backbone traces taken from images at 0.5 second intervals at 25° C. are displayed in FIG. 13. At 25° C., as MW is increased there is an increase in $l_p$ from 0.9±0.3 µm for EL2-10 to 14.0±2.9 µm for EL19-70, FIG. 13 top curve. This MW dependent increase in $l_p$ is still observed when the temperature is raised above the $T_g$ of the polymers to 37° C., however the absolute value of the persistence length is reduced for all preparations, FIG. 3 bottom curve. At this temperature, $l_p$ still increased with increasing polymer MW from 0.6±0.09 µm to 1.8±0.5 µm for EL2-10 and EL 19-70, respectively.

f-PNC cross-sectional diameters by electron microscopy and temperature-sensitive effective diameters by light scattering were MW dependent. Electron micrographs of the different PNC preparations further verified their filamentous structure (data not shown). The different MW filaments were free of branching and no spherical population was detected. In this sense, they were relatively homogeneous, but there were distinct differences. Specifically, from the TEMs, line scans across the f-PNC revealed their cross sectional diameters increased with increasing MW, although this phenomena appeared to be nearing saturation as the two highest polymer MWs were obtained, FIG. 14A. The narrowest filaments were from polymer EL2-10 with cross sectional diameters, d, of approximately 26.8±1.4 nm. EL19-70 revealed the widest f-PNC with cross sections of 121.1±3.6 nm.

Figure 14B:
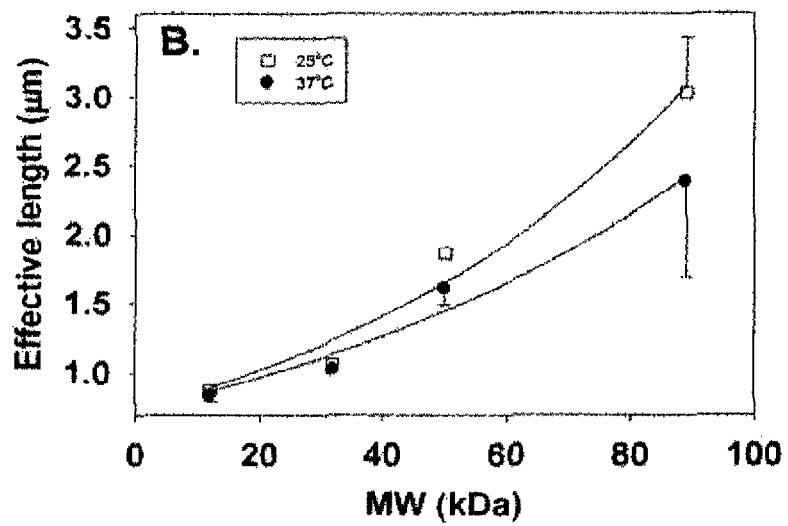
FIG. 14B shows effective length, from DLS, as a function of polymer MW. DLS built-in heating stage controlled temperature, set at 25° C. (□) or 37° C. (●).

Further verification of the MW and temperature sensitivity of the f-PNC flexibility was noted via dynamic light scattering (DLS) experiments, FIG. 14B. Diffusion coefficients of the samples were measured by DLS and the effective lengths were thus determined from a modified Stokes-Einstein equation for diffusion:

$$D = \frac{k_B T}{2 \pi \eta L_{Eff}} \qquad \text{(ii)}$$

where D is the diffusion coefficient, $k_B$ is the Boltzmann constant, T is the sample temperature, $\eta$ is the temperature-dependent viscosity (predicted by the Brookhaven DLS), and $L_{Eff}$ is the effective length (Cai et al 2007, cited above; Li et al, 2004 cited above). Equation (ii) was derived initially to predict the effective length of rigid rods, but has been suitable enough for the approximation of effective lengths of flexible filaments.[15, 16] A built-in heating stage in the DLS provided sample temperature control. At 25° C. (FIG. 14B, top curve, white squares) the $L_{Eff}$ increases with MW from 873.7±30.1 nm for EL2-10 to 3028.8±397.9 nm for EL19-70. Similar to results observed from fluorescence data, when the temperature is increased above the $T_g$ of the polymer materials to 37° C. (FIG. 14B, bottom curve, black circles), the effective length decreases for all preparations. The overall trend is still one of increasing $L_{Eff}$ with increasing MW, where EL2-10 is 838.6±41.9 nm and EL19-70 is 2375.4±690.4 nm.

Figure 15A:
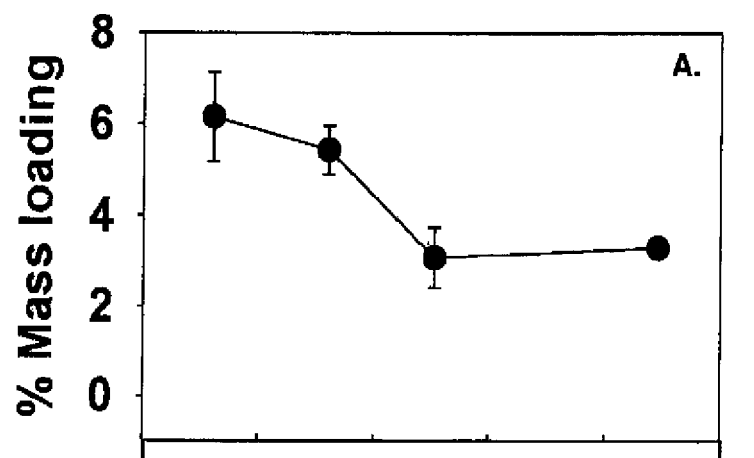
FIGS. 15A-15C show therapeutic enzyme loading, particle mass yield, and resistance to proteolytic degradation upon f-PNC encapsulation.
Figure 15B:
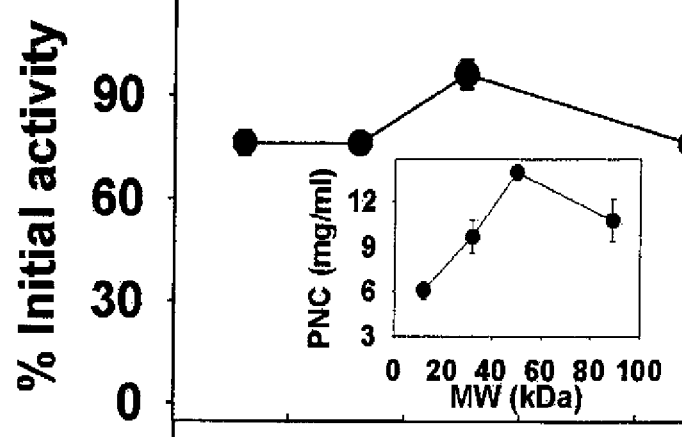
Figure 15C:
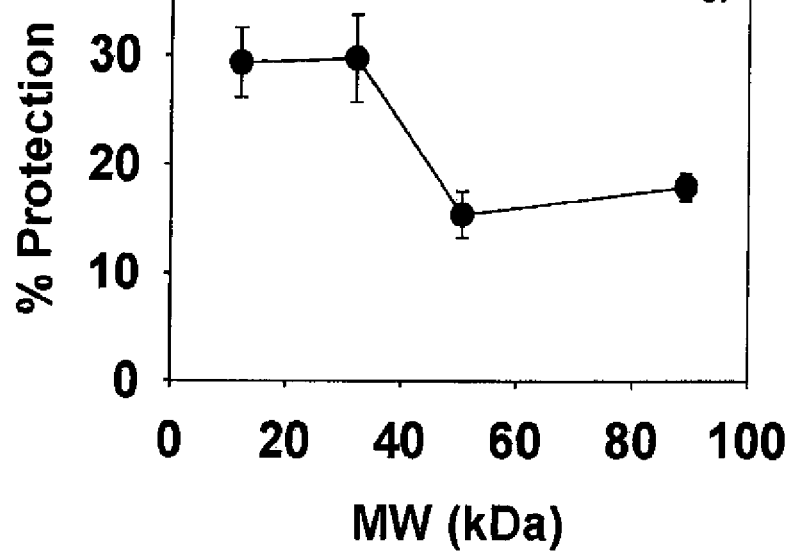

Polymer filaments of different MW load active enzyme that is resistant to protease degradation upon encapsulation. Loading of catalase into f-PNC and subsequent enzymatic activity was characterized, along with the resistance of the enzyme to degradation by proteases, as described in preceding examples. First, $^{125}$I-labeled catalase was traced in order to determine the mass loading of the enzyme into the nano-fraction of formulated f-PNC (any larger micron sized aggregates were removed during the first purification step, described above). The loading efficiency, or percent of loading by enzyme mass (defined as the percent of catalase added to the initial emulsion that is loaded into f-PNC), is indicated in FIG. 15A as a function of MW. While there are no evident loading dependencies on polymer MW, all filamentous preparations loaded comparable amounts of catalase, similar to filament loading efficiencies described above. The highest loading efficiency occurred with EL2-10 at 6.1±1.0%, or approximately 6.1 µg of catalase per f-PNC preparation, while the lowest efficiency was 3.1±0.7%, or 3.1 μg per f-PNC preparation.

Formulation-induced catalase inactivation, i.e., retention of enzymatic activity post-preparation of the nanofilaments, was determined, FIG. 15C. This degree of apparent enzyme inactivation during the encapsulation within f-PNC was similar for each polymer MW, and was relatively mild compared to formulations in preceding examples. Post-formulation specific enzymatic activities, i.e., Units of activity/mg of protein, ranged from 76.2±2.0% (EL5-27) to 96.1±4.1% (EL10-40) of the original stock catalase, before processing.

Enzymatic activity per f-PNC preparation was normalized, where we defined percent loading as:

$$\%\text{ Loading} = \left(\frac{\text{activity recovered in } PNC}{\text{total activity, post formulation}}\right) \times (\%\text{ apparent catalase inactivation}) \quad \text{(iii)}$$

where % apparent catalase inactivation factors in activity lost during the formulation process described in above examples. This measurement is more indicative of the specific enzymatic activity physically present with each f-PNC sample, since there is often some variation in inactivation between preparations. Significant activity loading occurred with all preparations, but there is no statistically significant difference in activity loading between different polymer MWs. Activity loading was 5.3±3.7% and 9.3±6.1% for EL5-27 and EL10-40, respectively.

Quantitative analysis of PEG content from a colorimetric assay revealed the final f-PNC mass yield in the nano-scale fraction of the particles. From the following equation based on the equimolar existence of PEG and PLA in the polymer diblock:

$$\text{Diblock polymer mass yield} = \left\{\frac{x(\text{g}, PEG)}{MW_{PEG}(\text{g/mol}, PEG)} \times [MW_{PLA}(\text{g/mol}, PLA)]\right\} + [x(\text{g}, PEG)] \quad \text{(iv)}$$

From equation (iv), f-PNC mass yield, and thus concentration, was determined. There was a slight increasing trend in yield with increasing MW, although this seemed to actually decrease slightly for the highest MW polymer, EL19-70, FIG. 15B inset. The lowest yield was from EL2-10 PNC at 6.0±0.6 mg/ml, while the highest yield occurred with the polymer EL10-40 at 13.9±0.5 mg/ml.

Assessment of resistance of the encapsulated enzyme to protease (e.g., pronase) degradation represents another means to quantify the quality of catalase encapsulation (see above examples, Dziubla 2005 and 2008, both cited above). In other words, f-PNC protection of catalase helps differentiate truly encapsulated drug from drug that is surface adsorbed, or near the surface of the particle and potentially susceptible to external protease denaturation. Percent protection, or the amount of protein resistant to protease degradation relative to the total protein loaded into f-PNC, after a one hour incubation with pronase ranged between 15.4±2.1% for EL10-40 and 29.7±4.0% for EL5-27, FIG. 15B. This is in contrast to non-PNC encapsulated catalase preparations where loading was through pure surface adsorption and protective effect was less than 5% as described in above examples.

In this example, the polymer MW control of two unique features of the particle formulation utilized were demonstrated. First, through maintenance of comparable ratios of hydrophobic to hydrophilic domains in the polymer, regardless of the absolute MW, enzyme-loaded filamentous PNC are possible. Second, the above-mentioned parameter of carrier stiffness is MW-tunable, i.e., increasing MW increases f-PNC flexibility in solution. Similarly, the contour lengths and cross sectional diameters of the f-PNC demonstrated polymer MW dependence, analogous to the MW-stiffness relationship. It should be noted that in addition to polymer MW reduction, sonication can also be utilized to reduce the length of these filamentous carriers (data not shown).

The MW-tunable stiffness phenomenon is closely related to the inherent thermal properties of the polymer. As revealed by DSC, the $T_g$ for the polymers tested are all just above room temperature. When heated above the $T_g$, there is a noticeable increase in carrier flexibility. Initially observed by time-resolved fluorescence microscopy, this effect was mirrored by DLS. Interestingly, the 37° C. curves from FIGS. 13 and 14B, when plotted on the same scale axes, are actually quite similar. Although the trend is increased effective length by DLS with increasing MW at 25° C. (FIG. 14B), similar to enhanced persistence length (FIG. 13), the absolute values do not correlate one to one. This is potentially due to limitations in the DLS equipment, which according to the manufacturer (Brookhaven Instruments) is designed to reliably measure particles only up to two to three microns. As can be seen by the persistence lengths in FIG. 13, these values are notably exceeded for higher MW preparations and thus may fall out of range of the DLS.

In another unexpected result, the mass yield increased with increasing MW, except for the highest MW, EL19-70, FIG. 14C. The polymer compositions, or % PLA, were similar between all preparations and adequate to produce filamentous PNC. However, the actual % PLA is slightly less for EL19-70 than EL10-40 (Table 3), which may reduce the f-PNC mass yield, as a similar result was observed in the above examples with decreasing % PLA.

Some interesting comparisons can be made with filamentous micelles (filomicelles) made from similar materials but formulated with different techniques (Geng 2006 cited above). Importantly, it should be noted that the self-assembled filomicelles (AKA worm micelles) in question were prepared with a cosolvent/evaporation technique, while the non-self-assembled carriers of Example 14 were synthesized with a modified double emulsion. Filomicelles can be made from several different amphiphilic diblock copolymers, but perhaps the most appropriate comparison would be with those made from PEG-PCL (polycaprolactone), a poly(ether-b-ester), similar to PEG-PLA. One key difference in the material that should be noted is the difference in hydrophobicity; PCL is often considered much more hydrophobic than PLA. Regardless, filomicelles have been shown to have a similar persistence length and cross sectional diameter dependence on polymer MW (Dalhaimer 2006 cited above). Furthermore, PEG-PCL filomicelles, although typically made from lower MW polymers than utilized in Example 14, do have comparable persistence lengths to the PEG-PLA carriers reported (Geng 2006 cited above). For example, a 4.7 kDa PEG-PCL filomicelle has an $l_p$ of ~500 nm while a higher MW version, 11.5 kDa, registers at ~5 microns. The closest PEG-PLA polymer for comparison from this study would be EL2-10 (~12 kDa) which forms filaments with an $l_p$ of ~900 nm, FIG. 13. The much higher PEG-PLA MWs used here explain the notably higher cross-sectional diameters observed, relative to filomicelles. For instance, increasing PEG-PCL MW from 4.7 kDa to 11.5 kDa resulted in an increase of diameter from ~11 nm to ~29 nm. Similarly, EL2-10 (12.1 kDa) f-PNC had d~27 nm, yet EL19-70 (89.1 kDa) had d~121 nm, FIG. 14A.

The MW-tunable stiffness phenomenon is closely related to the inherent thermal properties of the polymer. As revealed by DSC, the $T_g$ for the polymers tested are all just above room temperature. When heated above the $T_g$, there is a noticeable increase in carrier flexibility. Initially observed by time-resolved fluorescence microscopy, this effect was mirrored by DLS. Interestingly, the 37° C. curves from FIGS. 13 and 14B, when plotted on the same scale axes, are actually quite similar. Although the trend is increased effective length by DLS with increasing MW at 25° C. (FIG. 14B), similar to enhanced persistence length (FIG. 13), the absolute values do not correlate one to one. This is potentially due to limitations in the DLS equipment, which according to the manufacturer (Brookhaven Instruments) is designed to reliably measure particles only up to two to three microns. As can be seen by the persistence lengths in FIG. 13, these values are notably exceeded for higher MW preparations and thus may fall out of range of the DLS.

In another unexpected result, the mass yield increased with increasing MW, except for the highest MW, EL19-70, FIG. 14C. The polymer compositions, or % PLA, were similar between all preparations and adequate to produce filamentous PNC. However, the actual % PLA is slightly less for EL19-70 than EL10-40 (Table 3), which may reduce the f-PNC mass yield, as a similar result was observed in the preceding examples with decreasing % PLA.

All publications, including any priority applications, cited in this specification are incorporated herein by reference. It will be appreciated that modifications can be made from the compositions and methods described herein without departing from the spirit of the invention embodied in the claims. Such modifications are intended to fall within the scope of the appended claims.

The invention claimed is:

1. A method of making a filamentous polymeric nanocarrier that encapsulates a biologically active protein and protects it from proteolysis, the method comprising:
    (a) forming a primary emulsion using a freeze-thaw cycle of:
        (i) an amphiphilic diblock copolymer, which has a molecular weight of about 10,000 to about 100,000 Da and comprises a conjugate of a hydrophobic polymer block and a hydrophilic polymer block, wherein said amphiphilic diblock copolymer comprises greater than 81% to about 95% by weight of said hydrophobic polymer block; and
        (ii) a biologically active protein which is modified by attachment of polyethylene glycol; and
    (b) forming a secondary emulsion from said primary emulsion, and
    (c) recovering filamentous polymeric nanocarrier-encapsulated protein particles from said secondary emulsion, wherein said filamentous particles have a diameter of less than 70 nm and a length of from about 1 to about 50 microns, wherein said encapsulated protein is biologically active and protected from proteolysis.

2. The method according to claim 1 wherein said protein has a molecular weight of up to or equal to about 300,000 Da.

3. The method according to claim 2, wherein said amphiphilic diblock copolymer has a molecular weight of about 10,000 to about 40,000 Da.

4. The method according to claim 1, further comprising conjugating an affinity moiety to the surface of said polymeric nanocarrier particles.

5. The method according to claim 1, wherein the hydrophilic polymer is a modified or unmodified polyethylene glycol.

6. The method according to claim 1, wherein the polyethylene glycol conjugated to the protein is selected from the group consisting of methoxypolyethylene glycol, amine modified polyethylene glycol, biotinylated polyethylene glycol, and an alkyne terminated polyethylene glycol.

7. The method according to claim 1, wherein the hydrophobic polymer is selected from the group consisting of a poly(lactic acid) polymer and a polycaprolactone polymer.

8. A composition comprising polymeric nanocarrier particles prepared according to the method of claim 1.

9. A composition comprising polymeric nanocarrier particles prepared according to the method of claim 2.

10. A composition comprising polymeric nanocarrier particles prepared according to the method of claim 3.

11. A composition comprising polymeric nanocarrier particles prepared according to the method of claim 4.

12. A composition comprising polymeric nanocarrier particles prepared according to the method of claim 6.

13. A composition comprising polymeric nanocarrier particles prepared according to the method of claim 5.

14. A composition comprising polymeric nanocarrier particles prepared according to the method of claim 7.

* * * * *